(12) United States Patent
McCready et al.

(10) Patent No.: US 11,542,564 B2
(45) Date of Patent: Jan. 3, 2023

(54) COMPUTER-IMPLEMENTED METHOD, COMPUTER PROGRAM PRODUCT AND HYBRID SYSTEM FOR CELL METABOLISM STATE OBSERVER

(71) Applicant: Sartorius Stedim Data Analytics AB, Umeå (SE)

(72) Inventors: Christopher McCready, London (CA); Nicholas Trunfio, Billerica, MA (US)

(73) Assignee: Sartorius Stedim Data Analytics AB, Umeå (SE)

(*) Notice: Subject to any disclaimer, the term of this patent is extended or adjusted under 35 U.S.C. 154(b) by 379 days.

(21) Appl. No.: 16/796,340

(22) Filed: Feb. 20, 2020

(65) Prior Publication Data

US 2021/0262047 A1 Aug. 26, 2021

(51) Int. Cl.
C12Q 3/00 (2006.01)
(52) U.S. Cl.
CPC ..................... *C12Q 3/00* (2013.01)
(58) Field of Classification Search
CPC ...... G05B 13/048; G16B 40/00; C12M 41/38; C12M 41/30; C12M 41/48; C12Q 3/00
See application file for complete search history.

(56) References Cited

U.S. PATENT DOCUMENTS

| | | | | |
|---|---|---|---|---|
| 5,442,562 A * | 8/1995 | Hopkins | ................ | G05B 21/02 700/28 |
| 5,469,361 A * | 11/1995 | Moyne | ............ | G05B 19/41845 700/95 |
| 7,062,417 B2 * | 6/2006 | Kruger | .................... | G06F 17/18 703/2 |

(Continued)

FOREIGN PATENT DOCUMENTS

| | | |
|---|---|---|
| EP | 2169048 B1 | 3/2018 |
| WO | 2018185052 A1 | 10/2018 |

(Continued)

OTHER PUBLICATIONS

International Search Report and Written Opinion dated May 7, 2021 for International Application No. PCT/EP2021/050743.

(Continued)

*Primary Examiner* — Shogo Sasaki
(74) *Attorney, Agent, or Firm* — Wolf, Greenfield & Sacks, P.C.

(57) ABSTRACT

Techniques for predicting an amount of at least one biomaterial produced or consumed by a biological system in a bioreactor are provided. Process conditions and metabolite concentrations are measured for the biological system as a function of time. Metabolic rates for the biological system, including specific consumption rates of metabolites and specific production rates of metabolites are determined. The process conditions and the metabolic rates are provided to a hybrid system model configured to predict production of the biomaterial. The hybrid system model includes a kinetic growth model configured to estimate cell growth as a function of time and a metabolic condition model based on metabolite specific consumption or secretion rates and select process conditions, wherein the metabolic condition model is configured to classify the biological system into a metabolic state. An amount of the biomaterial based on the hybrid system model is predicted.

21 Claims, 33 Drawing Sheets

(56) References Cited

U.S. PATENT DOCUMENTS

| | | | |
|---|---|---|---|
| 7,107,491 B2 * | 9/2006 | Graichen | G06F 11/008 714/48 |
| 9,069,345 B2 | 6/2015 | McCready et al. | |
| 9,541,471 B2 | 1/2017 | McCready | |
| 2009/0164171 A1 * | 6/2009 | Wold | G06F 17/18 702/179 |
| 2009/0287320 A1 * | 11/2009 | MacGregor | G05B 17/02 700/29 |
| 2010/0191361 A1 * | 7/2010 | McCready | G05B 13/048 703/2 |
| 2022/0228097 A1 * | 7/2022 | White | C12M 41/44 |
| 2022/0228102 A1 * | 7/2022 | Le | G16B 40/00 |

FOREIGN PATENT DOCUMENTS

| | | |
|---|---|---|
| WO | WO 2019/070517 A1 | 4/2019 |
| WO | WO 2019/129891 A1 | 7/2019 |

OTHER PUBLICATIONS

International Search Report and Written Opinion dated May 21, 2021 for International Application No. PCT/EP2021/054206.
Gnoth et al., Control of cultivation processes for recombinant protein production: a review. Bioprocess and biosystems engineering. Jan. 2008;31(1):21-39.
Hausmann et al., Present Status of automation for industrial bioprocesses. In Current developments in biotechnology and bioengineering Jan. 1, 2017;725-57.
Krämer et al., A hybrid approach for bioprocess state estimation using NIR spectroscopy and a sigma-point Kalman filter. Journal of Process Control. Oct. 1, 2019;82:91-104.
Solle et al., Between the poles of data-driven and mechanistic modeling for process operation. Chemie Ingenieur Technik. May 2017;89(5):542-61.
Kornecki et al., "Accelerating Biologies Manufacturing by Upstream Process Modelling", Processes (2019), 7:166, 17 pages.
Velugula-Yellela et al., "Use of High-Throughput Automated Microbioreactor System for Production of Model IgG1 in CHO Cells", Journal of Visualized Experiments, Sep. 2018, 8 pages.
Wold et al., "PLS-regression: a basic tool of chemometrics", Chemometrics and Intelligent Laboratory Systems, 58 (2001), 22 pages.
MacGregor et al., "Data-based latent variable methods for process analysis, monitoring and control", Computers and Chemical Engineering 29 (2005), 7 pages.
Wold et al., "Principal Component Analysis", Chemometrics and Intelligent Laboratory Systems, 2 (1987) 16 pages.
Kourti, "Application of latent variable methods to process control and multivariate statistical process control in industry", Int. J. Adapt. Control Signal Process (2005); 19: pp. 213-246.

* cited by examiner

| BATCH | pH | TEMP | FEED | FINAL TITER (mg/L) |
|---|---|---|---|---|
| 1 | CENTER | 37.5 °C @ DAY 6 | CENTER | 2475.5 |
| 2 | 7.3 @ DAY 8 | 34 °C @ DAY 5 | LOW @ DAY 7 | 2626 |
| 3 | CENTER | CENTER | CENTER | 2912 |
| 4 | CENTER | CENTER | LOW @ DAY 7 | 2982 |
| 5 | 7.2 @ DAY 8 | 33 °C @ DAY 6 | CENTER | 2339 |
| 6 | CENTER | 34 °C @ DAY 7 | CENTER | 2252.5 |
| 7 | CENTER | CENTER | CENTER | 2952.5 |
| 8 | CENTER | CENTER | CENTER | 2965.5 |
| 9 | CENTER | 33 °C @ DAY 8 | LOW @ DAY 7 | 2137.5 |
| 10 | 7.3 @ DAY 6 | CENTER | LOW @ DAY 7 | 2628.5 |
| 11 | 7.3 @ DAY 6 | CENTER | CENTER | 3025 |
| 12 | CENTER | 35 °C @ DAY 6 | LOW @ DAY 7 | 2482.5 |

CENTER TARGETS
- pH: 7.1
- TEMP: 36.8 °C
- FEED: ADDITION OF GLUCOSE TO TARGET 2.5 g/l AT NEXT FEEDING

FIG.10

COMPUTER-IMPLEMENTED METHOD, COMPUTER PROGRAM PRODUCT AND HYBRID SYSTEM FOR CELL METABOLISM STATE OBSERVER

FIELD OF THE INVENTION

The application relates to a computer-implemented method, a computer program product, and a system for a cell metabolism state observer comprising a hybrid model, and in particular, a hybrid model that may be used to provide observability into metabolism of the bioreactor and/or optimize bioprocess reaction conditions.

BACKGROUND

In biomanufacturing, biological systems are orchestrated to produce a specific biomaterial. This process typically involves placing cells and/or microbes into a bioreactor with media containing essential nutrients under controlled atmospheric conditions. The media is consumed by the cells and used for growth and other metabolic functions, including production of the specific biomaterial and production of byproducts.

The bioreactor contains instrumentation that continuously (e.g., once every second or minute) measures process conditions, such as temperature, pH, and dissolved oxygen, as well as addition of nutrients and gasses, and flow and content of streams leaving the bioreactor. Typically, samples of the bioprocess are taken periodically (e.g., once or twice per day, or more) that measure the content of the bulk fluid, including metabolites (e.g., glucose, glutamine, lactate, NH4, etc.), as well as cell concentrations, concentration of the product biomaterial (also referred to as titer), and the concentration of quality attributes (e.g., byproducts, etc.). However, these approaches rely on indirect measurements of the average cell's metabolic behavior.

Techniques for modeling and analyzing cell behavior include flux balance analysis (FBA), which may be used to model and analyze cell metabolic behavior from specific consumption and specific production of the measured metabolites. FBA calculates the flow of specific metabolites through a metabolic network, allowing prediction of growth rate of an organism or rate of production of a metabolite. In order to prevent model over-fitting, this type of analysis requires specific genetic knowledge of the cell line in the bioreactor process, along with measurements of gene-expression and metabolite levels beyond what is normally measured during process development and manufacturing activities. In general, observation of cell metabolism is extremely limited during process development and manufacturing, which limits use of this approach.

In other cases, statistical methods have value in building regression models to correlate measured process conditions and metabolites to predict titer and byproducts. These methods, while beneficial for predictive purposes, have limited ability with regard to understanding which of the process variables (e.g., related to the metabolic function) are responsible for good performance.

In still other aspects, models such as Monod kinetics models have been used to predict cell growth. This type of model effectively predicts growth rates of cells, based on concentrations of substrate(s) and inhibitory metabolites. However, this approach also does not consider the current state of the cell.

Accordingly, lack of direct measurements of metabolic activity during process development creates a scenario wherein trial and error is used to design process operations. Using this approach, experiments are conducted, in an ad hoc manner, to determine conditions that produce high quality product with a relatively high yield.

Development of process understanding is challenging, and the ability to diagnose strange behaviours or optimize processes is difficult. Often, biologically relevant hypotheses for which metabolic state(s) could result in the observed metabolite profiles is left to subject matter experts (SMEs).

Monitoring of biological manufacturing processes is also challenging. Typically, control charts are generated for important process parameters and metabolites. This assures that the process is in-control relative to normal operation but does not monitor the biological cell metabolism. Diagnosis or prediction of abnormal metabolic operation is again left to the SMEs.

Traditional fed-batch processes operate at relatively safe conditions with nutrients in abundance, resulting in titers typically around 2-6 g/L. To optimize productivity (e.g., product formation) to achieve higher titers (e.g., 20 g/L and above), longer run times may be needed, but this may also lead to higher production of byproducts. However, absent knowledge of cell metabolism, optimizing productivity is difficult and is performed in an ad hoc manner.

SUMMARY

According to an aspect of the invention, computer-implemented methods, computer program products, and systems are provided for a cell metabolism state observer comprising a hybrid model to optimize bioprocess reaction conditions. From a process control perspective, observability of cell metabolism allows the bulk fluid to be maintained at correct conditions, e.g., control nutrients in the bulk fluid, in order to maximize metabolic activity towards production of product while minimizing undesirable activity (e.g., formation of byproducts, excessive cell growth, etc.). Observability, a term from advanced process control, refers to the ability to generate visibility into a measured, or in this case unmeasured, underlying driver of a system (e.g., bioreactor).

According to an aspect, a computer-implemented method using a cell metabolism state observer for predicting an amount of at least one biomaterial produced or consumed by a biological system in a bioreactor is provided. The method includes:

measuring process conditions and metabolite concentrations for the biological system as a function of time;

determining metabolic rates for the biological system, including specific consumption rates of metabolites and specific production rates of metabolites;

providing the process conditions and the metabolic rates to a hybrid system model configured to predict production of the biomaterial, the hybrid system model comprising:

a kinetic growth model configured to estimate cell growth as a function of time; and a metabolic condition model based on metabolite specific consumption or secretion rates, select process conditions, wherein the metabolic condition model is configured to classify the biological system into a metabolic state; and predicting an amount of the biomaterial based on the hybrid system model.

The metabolic condition model, when used in a real-time context, is a type of state observer.

Further, in the method according to the above-stated aspect, the kinetic growth model may be configured to estimate viable cell density.

Further, in the method according to the above-stated aspect, the kinetic growth model may be configured to account for lysed cells.

Further, in the method according to the above-stated aspect, a metabolic state observer may be constructed for a metabolite to provide an estimate of an internal metabolic state of the biological system.

Further, in the method according to the above-stated aspect, the method may comprise:
obtaining a current measurement of the metabolite;
determining a consumption rate for the metabolite using the metabolic state observer; and
predicting a future concentration of the metabolite using the metabolic state observer and the current measurement.

Further, in the method according to the above-stated aspect, cell state classification may be performed using the metabolic state observer to estimate specific consumption rates or specific production rates for the metabolite.

Further, in the method according to the above-stated aspect, the estimated specific consumption rates or the estimated specific production rates are determined using training data.

Further, in the method according to the above-stated aspect, the method may further comprise:
classifying the internal metabolic state into an optimal or a suboptimal category for biomaterial production; and
sending a notification to a user, when the internal metabolic state is classified into a suboptimal category.

Further, in the method according to the above-stated aspect, the kinetic growth model comprises a Monod kinetic model or a saturation kinetic model.

Further, in the method according to the above-stated aspect, cell density or cell viability for the biological system may be measured as a function of time.

Further, in the method according to the above-stated aspect, the kinetic growth model is further configured to estimate microbial cell growth as a function of time.

Further, in the method according to the above-stated aspect, the metabolic condition model may comprise one or more of a machine learning model, a deep learning model, a principal component analysis (PCA) model, a partial least squares (PLS) model, a partial least squares discriminant analysis (PLS-DA) model, or an orthogonal partial least squares discriminant analysis (OPLS-DA) model.

Further, in the method according to the above-stated aspect, a test sample may be obtained from the bioreactor, and the method may determine whether the amount of the biomaterial in the test sample is within a range predicted by the hybrid system model.

Further, in the method according to the above-stated aspect, parameters of the hybrid system model may be updated when the hybrid system model is in operation, such that the parameters include the metabolic rates and coefficients associated with the hybrid system model.

Further, in the method according to the above-stated aspect, the process conditions may include one or more of pH, temperature, dissolved oxygen, osmolality, process flow leaving the bioreactor, growth media, by-products, amino acids, metabolites, oxygen flow rate, nitrogen flow rate, carbon dioxide flow rate, air flow rate, and agitation rate.

Further, in the method according to the above-stated aspect, the growth media or feed may comprise nutrients including an amino acid, a saccharide, or an organic acid.

Further, in the method according to the above-stated aspect, the by-products of the bioprocess may include an amino acid, a saccharide, an organic acid, or ammonia.

Further, in the method according to the above-stated aspect, the method may further comprise:
determining optimal process conditions for the bioreactor based on the hybrid system model;
measuring experimental process conditions of the bioreactor using one or more sensors as a function of time;
monitoring the measured experimental process conditions to detect deviations from the optimal process conditions; and
when a deviation is detected, sending a notification to a user.

Further, in the method according to the above-stated aspect, the method may further comprise:
determining optimal process conditions for the bioreactor based on the hybrid system model;
measuring experimental process conditions of the bioreactor using one or more sensors as a function of time;
monitoring the measured experimental process conditions to detect deviations from the optimal process conditions; and
providing feedback to a controller controlling the bioreactor to automatically adjust the experimental process conditions to minimize deviation from the optimal process conditions.

In some aspects, the method may further comprise:
determining optimal process conditions for the bioreactor based on the hybrid system model;
measuring experimental process conditions of the bioreactor using one or more sensors as a function of time;
monitoring the measured experimental process conditions to detect deviations from the optimal process conditions;
sending a notification to a user when a deviation is detected; and
providing feedback to a controller controlling the bioreactor to automatically adjust the experimental process conditions to minimize deviation from the optimal process conditions.

Further, in the method according to the above-stated aspect, the method may further comprise:
simulating, using the hybrid system model, a predicted amount of at least one biomaterial, wherein the hybrid system model is initialized with the process conditions; and
determining one or more states of the biological system based on the simulation.

Further, in the method according to the above-stated aspect, the method may further comprise adjusting the process conditions based on an optimization method to determine a set of process conditions that optimize predicted trajectories, product quantity (titer), and/or product quality.

In another aspect, the method comprises calibrating a hybrid system model for predicting a biomaterial produced in a bioreactor by a biological system comprising:
obtaining experimental data including measurement of one or more process conditions, one or more metabolite concentrations, and a cell amount for a plurality of bioreactor batches, each batch associated with a specific set of process conditions;
determining a growth rate under ideal conditions, using a kinetic model of the hybrid system model, based on the experimental data;
determining a cell lysis parameter, using the kinetic model, based on the growth rate under the ideal conditions and the growth rate from the experimental data;
determining specific production rates or specific consumption rates of metabolites;
determining kinetic parameters for factors that inhibit growth to minimize differences between the growth rate under the ideal conditions and the growth rate from the experimental data; and providing the determined kinetic parameters, the cell lysis parameter, the growth rate, and the specific production rates or the specific consumption rates of the metabolites to a metabolic condition model of the hybrid system model for classification of the biological system into a metabolic state associated with specific productivity of the biomaterial produced by the biological system, based on measured specific consumption or measured secretion rates of the metabolites.

Further, in the method according to the above-stated aspect, a set of parameters may be provided to an optimization module, wherein the set of parameters includes the growth rate under the ideal conditions, the specific consumption rates and the specific production rates of metabolites, and new process conditions, to determine process conditions to optimize production of the biomaterial.

Further, in the method according to the above-stated aspect, the method may comprise monitoring bulk properties of the bioreactor using principal component analysis (PCA).

Further, in the method according to the above-stated aspect, an output of the bioreactor may be predicted using partial least squares (PLS) regression.

Further, in the method according to the above-stated aspect, the output may be an amount of the biomaterial.

In the present disclosure, "biomaterial" may include a metabolite, a cell, a desired protein, an antibody, an immunoglobulin, a toxin, one or more by-products, a target molecule, or any other type of molecule manufactured using a bioreactor. There may be more than one biomaterial of interest including the product, a target biologic.

In the present disclosure, "factors that inhibit growth" may include a substrate limitation, a temperature or pH shift, or metabolites that inhibit growth.

In the present disclosure, "specific productivity" refers to the amount of product produced on a per cell basis.

In the present disclosure, "process optimization" refers to determining optimal adjustments or settings for a process. This is described in further detail in the detailed description below.

Metabolites may include any suitable analyte, including but not limited to: amino acids (e.g., alanine, arginine, aspartic acid, asparagine, cysteine, cysteine, glutamic acid, glutamine, glycine, histidine, hydroxyproline, isoleucine, leucine, lysine, methionine, phenylalanine, proline, serine, threonine, tryptophan, tyrosine, valine, etc.), saccharides (e.g., fucose, galactose, glucose, glucose-1-phosphate, lactose, mannose, raffinose, sucrose, xylose, etc.), organic acids (e.g., acetic acid, butyric and 2-hydroxy-butyric acids, 3-hydroxybutyric acid, citric acid, formic acid, fumaric acid, isovaleric acid, lactic acid, maleic acid, propionic acid, pyruvic acid, succinic acid, etc.), other organic compounds (e.g., acetone, ethanol, pyroglutamic acid, etc.)

The subject matter described in the application can be implemented as a method or as a system, and/or one or more computer program products. The subject matter described in the application can be implemented on a machine readable medium, wherein the medium is embodied in one or more information carriers, such as a CD-ROM, a DVD-ROM, a semiconductor memory, or a hard disk. Such computer program products may cause a data processing apparatus to perform one or more operations described in the application.

In addition, subject matter described in the application can also be implemented as a system including a processor, and a memory coupled to the processor. The memory may encode one or more programs to cause the processor to perform one or more of the methods described in the application. In some examples, the system may be a special purpose computer system including an embedded system.

BRIEF DESCRIPTION OF THE DRAWINGS

Details of one or more implementations are set forth in the exemplary drawings and description below. Other features will be apparent from the description, the drawings, and from the claims. It should be understood, however, that even though embodiments are separately described, single features of different embodiments may be combined to further embodiments.

FIG. 10 shows examples of various process runs to determine ideal parameters according to the present disclosure.

FIG. 13A shows a PCA score scatter plot providing observability of a metabolic disturbance caused by a depletion in glucose (e.g., predictions from the state observer using PCA). Glucose concentrations within the circle centered at the origin represent normal operation. However, glucose values outside of this range indicate increased risk of reduction in titer or product quality issues. FIG. 13B shows a PCA score scatter plot providing observability of variability in metabolic function resulting from transitions from exponential growth to stationary phase. This chart demonstrates an example of providing observability of variation in metabolic activity throughout the trajectory of a fed-batch process. FIG. 13C shows an example PCA loadings chart to assist in developing process understanding of the PCA score scatter plots (e.g., predictions from the state observer using PCA).

FIG. 14A shows the measured specific productivity from experimental data and the predicted specific productivity from a PLS metabolic condition model from the state observer (using PLS) (e.g., productivity, specific consumption, metabolites, u). FIG. 14B shows a PLS score scatter plot providing observability of metabolic variability related to variation in specific productivity from the state observer (using PLS) (e.g., productivity, specific consumption, metabolites, u). FIG. 14C shows the associated PLS loadings chart providing process understanding of the variables correlated with variability in specific productivity from the state observer (using PLS) (e.g., productivity, specific consumption, metabolites, u).

FIG. 15A shows an example of simulating the growth and titer (the concentration of the target product resulting from specific productivity) for a given starting condition and independent variable trajectory. Also included is the measured growth and titer data to compare the predicted versus measured results. FIG. 15B shows specific productivity from the state observer (using PLS) (e.g., productivity, specific consumption, metabolites, u).

FIG. 17A shows an example of the measured and predicted trajectories for a batch with a temperature shift (inhibits growth). FIG. 17B shows the measured and predicted trajectories for a batch with a pH shift and a low feed rate (glucose depletion). FIG. 17C shows the measured and predicted trajectories for a batch with a pH and temperature shift.

DETAILED DESCRIPTION OF EMBODIMENTS

In the following text, a detailed description of examples will be given with reference to the drawings. It should be understood that various modifications to the examples may be made. In particular, one or more elements of one example may be combined and used in other examples to form new examples.

Figure 1:
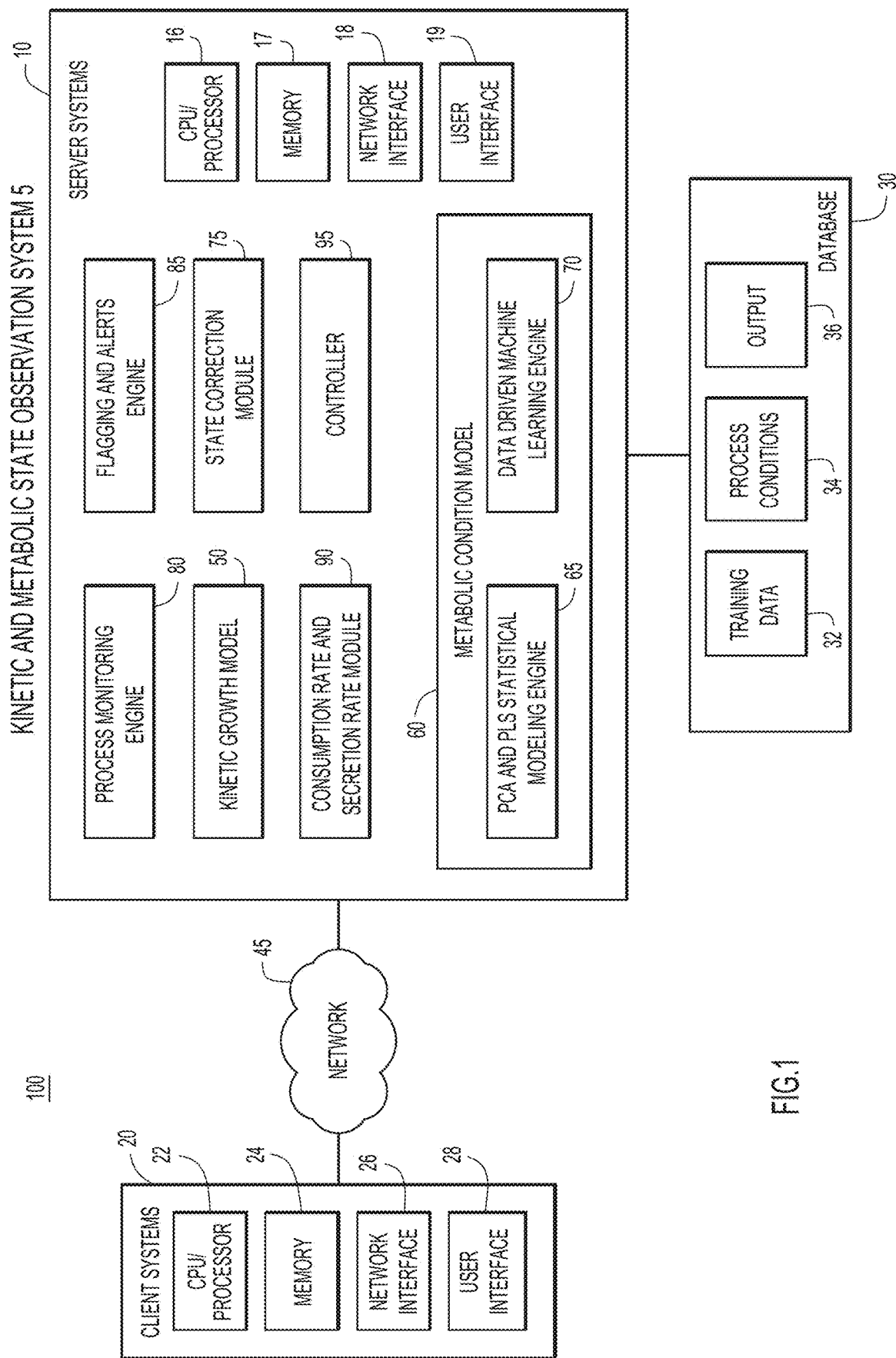
FIG. 1 shows an example of a computing environment for a hybrid model configured for cell metabolic state observation according to the present disclosure.

FIG. 1 shows a computing environment for the hybrid model described herein. The kinetic and metabolic state observation system 5 may comprise a plurality of specific processing modules, including a kinetic growth model 50, a metabolic condition model 60, a state correction model 75, a process monitoring engine 80, a flagging and alerts engine 85, and a consumption rate and secretion rate module 90. The metabolic condition model 60 may comprise additional modules, including a PCA and PLS statistical modeling engine 65 and a data-driven machine learning engine 70. Each of these components is described in additional detail as follows.

In particular, the hybrid model contains the kinetic growth model 50 and the metabolic condition model 60. The kinetic model determines amounts of live cells, lysed cells, viable cells, and cell density, etc. The metabolic condition model 60 provides product titer and quality control information about the titer and attributes (e.g., byproducts, etc.) about the bioprocess. In aspects, the output of the metabolic condition model 60 feeds into the kinetic growth model 50.

The hybrid model couples cell metabolism with metabolite material balances. In general, a metabolite is any analyte that the cells consume or secrete/generate. Existing bioprocess models may be constructed to predict the trajectory of biomaterial production, however, these bioprocess models are subject to uncertainty. Accordingly, the specific consumption and specific secretion rates for metabolites that are measured experimentally may not match the output of the bioprocess model. To resolve this uncertainty and reduce error, state correction model 75 may be used, which updates the estimate of the states of the kinetic growth model 50 only. An error may be derived based on differences between measured experimental output and estimated hybrid model output, and the parameters of the hybrid model may be adjusted based on the error signal (see also, FIG. 2) to drive the error signal to zero as a function of time.

Kinetic growth model 50 is a state observer based on the Monod growth equations (see, Eqs. 1-11) and metabolite material balance equations (see, Eqs. 12, 13). The Monod growth equations and metabolite material balance equations are a series of differential equations that may be used to describe cell growth (e.g., microbial cell growth), cell density and viable cell density, total cells (e.g., viable cells, dead cells and lysed cells), etc. Inputs to the kinetic growth model include temperature, feed conditions, pH, etc. and outputs include state estimates. In some aspects, the kinetic growth model is a classical state observer. In this context, parameters that are being modeled internally are referred to as states. For example, these parameters may include $x_v$, $x_d$, $x_l$, $m_i$.

Constructing a state observer from differential equations is known in the art. Accordingly, herein, such techniques have been extended to the Monod kinetic equations and metabolite material balance equations, which are a set of differential equations that describe cell growth and lifecycle in a biological cell culture and amounts of metabolites. Accordingly, the kinetic growth model may be used to monitor the number of live cells (and other parameters) in a bioreactor and to make predictions about the number of cells in the bioreactor at a future point in time. The Monod equations for growth for a bioreactor system with media exchange include the following equations:

$$x_t = x_v + x_d + x_l, \quad (1)$$

wherein $x_t$ is total cell density, $x_v$ is viable cell density, $x_d$ is dead cell density, and $x_l$ is lysed cell density;

$$\frac{dx_v}{dt} = \left(u_{eff} - u_d - \frac{F_b}{V}\right)x_v, \quad (2)$$

wherein $dx_v/dt$ corresponds to the change in viable cell density as a function of time, and $u_{eff}$ corresponds to an effective growth rate, $u_d$ is the cell death rate, $F_b$ is the cell bleed flow rate containing the same material as in the bioreactor and V is the volume of the material in bioreactor;

$$u_d = k_d + k_t x_l, \quad (3)$$

wherein $k_t$ is the increase in death rate due to lysed cell concentration representing the toxicity of the bulk fluid;

$$\frac{dx_l}{dt} = k_l x_d - \frac{(F_h + F_b)}{V} x_l; \quad (4)$$

wherein $k_l$ is the rate dead cells convert to lysed cells, $F_h$ is the harvest flow rate containing the bulk fluid (live and dead cells are separated from the fluid and recycled back into the bioreactor);

$$\frac{dx_d}{dt} = u_d x_v - \left(k_l + \frac{F_b}{V}\right)x_d; \quad (5)$$

$$u_{eff} = u_{max} \theta_{sub} \theta_{quad} \theta_{inh}, \quad (6)$$

wherein the effective cell density may be determined based on $u_{max}$ that corresponds to the maximum growth rate corresponding to the growth rate under optimal conditions, wherein $\theta_{sub}$ corresponds to reduction in growth rate due to substrate depletion, $\theta_{quad}$ corresponds to a reduction in growth rate due to quadratic terms (e.g., temp, pH, etc.) straying from target values where growth is maximized, and $\theta_{inh}$ corresponds to inhibition in growth due to the excess amount of a biomaterial (e.g., metabolite, cell density or independent variable);

$$\theta_{sub} = \Pi\left[\tanh\left(2\frac{s_i}{\theta_{s,i}}\right)\right]^2; \quad (7)$$

wherein $s_i$ is the substrate value, which may be a metabolite or independent variable, $\theta_{s,i}$ is a coefficient representing the substrate concentration below which growth is inhibited;

$$\theta_{quad} = \Pi\exp\left[-\frac{(q_i - \theta_{i,opt})^2}{\theta_{q,i}}\right]; \quad (8)$$

wherein $q_i$ is the value of the quadratic variable which may be a metabolite or independent variable, $\theta_{i,opt}$ is a coefficient representing the value of the quadratic variable where growth is maximized, and $\theta_{q,i}$ is a coefficient representing the sensitivity of the growth inhibition.

$$\theta_{inh} = \Pi\left[\left(\frac{I_i}{2\theta_{i,i}}\right)^3 + 1\right]^{-1}; \quad (9)$$

wherein $I_i$ is the value of the inhibition variable which may be a metabolite or independent variable, $\theta_{i,i}$ is a coefficient representing the value of the inhibition variable above which growth is inhibited.

$$\frac{dIgG}{dt} = Qp(m, \delta_{m,i}(t), u)x_v, \quad (10)$$

wherein $$\frac{dIgG}{dt}$$

is the rate of change of the biomaterial as a function of time, Qp is a function with inputs comprising metabolite concentrations m, $\delta_{m,i}(t)$ is the specific production or specific consumption rate of a metabolite at the current time, u is the independent variables, and $x_v$ is viable cell density;

$$\frac{dm_i}{dt} = \delta_{m,i}(t)x_v - \frac{(F_h + F_b)}{V}m_{r,i} + \frac{F_f}{V}m_{f,i}, \quad (11)$$

wherein $$\frac{dm_i}{dt}$$

is the rate of change of a metabolite, $\delta_{m,i}(t)$ is the specific consumption or secretion rate of a metabolite at the current time, $m_{r,i}$ is the concentration of a metabolite in the bioreactor, $m_{f,i}$ is the concentration of a metabolite in the feed and $F_f$ is the flow rate of the feed containing fresh media.

Outputs of the kinetic growth model include product titer, specific productivity/specific consumption, metabolite concentration, viable cell density, and viability.

The specific consumption (or secretion) rate for the given time or cell state $\delta_{m,i}(t)$ may be calculated from the training set (e.g., measured data using Eqs. 14 and 15), and using the following equations:

$$\delta_{m,i}(t_k) = \left(m_{i,k} - m_{i,k+1} + \frac{mAdd_{i,k}}{V_k}\right)iVCD^{-1} \quad (12)$$

$$iVCD = (0.6\, x_{v,k} + 0.4\, x_{v,k+1})(t_{k+1} - t_k) \quad (13)$$

These equations are defined below.

Metabolic condition model 60 classifies the internal metabolic state of the system, e.g., into an optimal or suboptimal state or category for biomaterial production. Optionally, input into the metabolic condition model may include temperature, feed conditions, etc. In general, the metabolic condition model is independent from the kinetic growth model, and metabolic condition monitoring may be performed independently of kinetic growth.

In some aspects, the metabolic condition model may be used to enhance the kinetic growth model by providing estimates of titer and/or quality to improve titer prediction.

The metabolic condition model contains at a minimum, metabolites and VCD to calculate specific consumption/specific production of metabolites. The metabolic condition model optionally contains additional measured parameters and/or unmeasured states to improve prediction of product titer and/or quality. In some embodiments, the metabolic condition model comprises a statistical modeling engine 65 for principal component analysis (PCA) or partial least squares (PLS) or orthogonal partial least squares (OPLS) of the specific consumption/production rates (and optionally, additional parameters measured from the process or states). This model starts with the metabolite specific consumption/secretion rates in FIG. 9A (component 720) and converts this to multivariate scores (T_cell state, component 730).

Statistical modeling engine may comprise any suitable engine, including (PCA) model, a partial least squares (PLS) model, a partial least squares discriminant analysis (PLS-DA) model, and/or an orthogonal partial least squares discriminant analysis (OPLS-DA) model.

PCA may be used to analyze bulk properties of the bioreactor (e.g., the system as a whole—titer), while PLS may be used to analyze specific metabolites (e.g., glucose), for example, to predict an output of the bioreactor. PCA is used to characterize metabolic variation without underlying context. PLS is used to correlate metabolic variation to productivity (titer) or production of an important quality metric (product quality). Techniques for performing PLS may be found, e.g., in Wold et al., PLS-regression: a basic tool of chemometrics, Chemometrics and Intelligent Laboratory Systems 58 (2001) 109-130. Techniques for performing PCA may be found, e.g., in Wold et al., Principal Component Analysis, Chemometrics and Intelligent Laboratory Systems 2 (1987) 37-52. Both PCA and PLS may be used to reduce dimensionality of a data set. PCA, a type of unsupervised dimension reduction technique, allows data to be summarized by linear combinations of variables without losing a significant amount of information. PLS, a type of supervised dimension reduction technique, is applied based on correlation between a dependent variable and independent variables. These techniques are considered to be within the scope of one of skill in the art.

In some aspects, the output of the metabolic condition model 60 feeds into the kinetic growth model 50. The metabolic condition model 60 may also allow visualization of the metabolic condition (state) of the cell metabolism. Therefore, the output of the metabolic condition model 60 serves as both an input to the kinetic growth model 50, as well as facilitates monitoring and visualization of the metabolic condition of the cell metabolism.

The metabolic condition model may contain or be linked to a data-driven machine learning engine 70 and/or a principal component analysis (PCA) and partial least squares (PLS) statistical modeling engine 65. In other aspects, the metabolic condition model may contain both statistical modeling engine 65 and data driven machine learning engine 70. Machine learning engine 70 may comprise a neural net, a deep learning model, or other machine learning model. Machine learning engine 70 may be trained using known techniques to classify the state of the biological system/bioreactor into an optimal or suboptimal state. Additionally, machine learning engine 70 may be trained using known techniques to classify the state of metabolite(s) into an optimal or suboptimal state. In aspects, machine learning engine 70 performs classifications comparable to statistical modeling engine 65, and in some cases, with higher accuracy and precision than statistical modeling engine 65.

Figure 2:
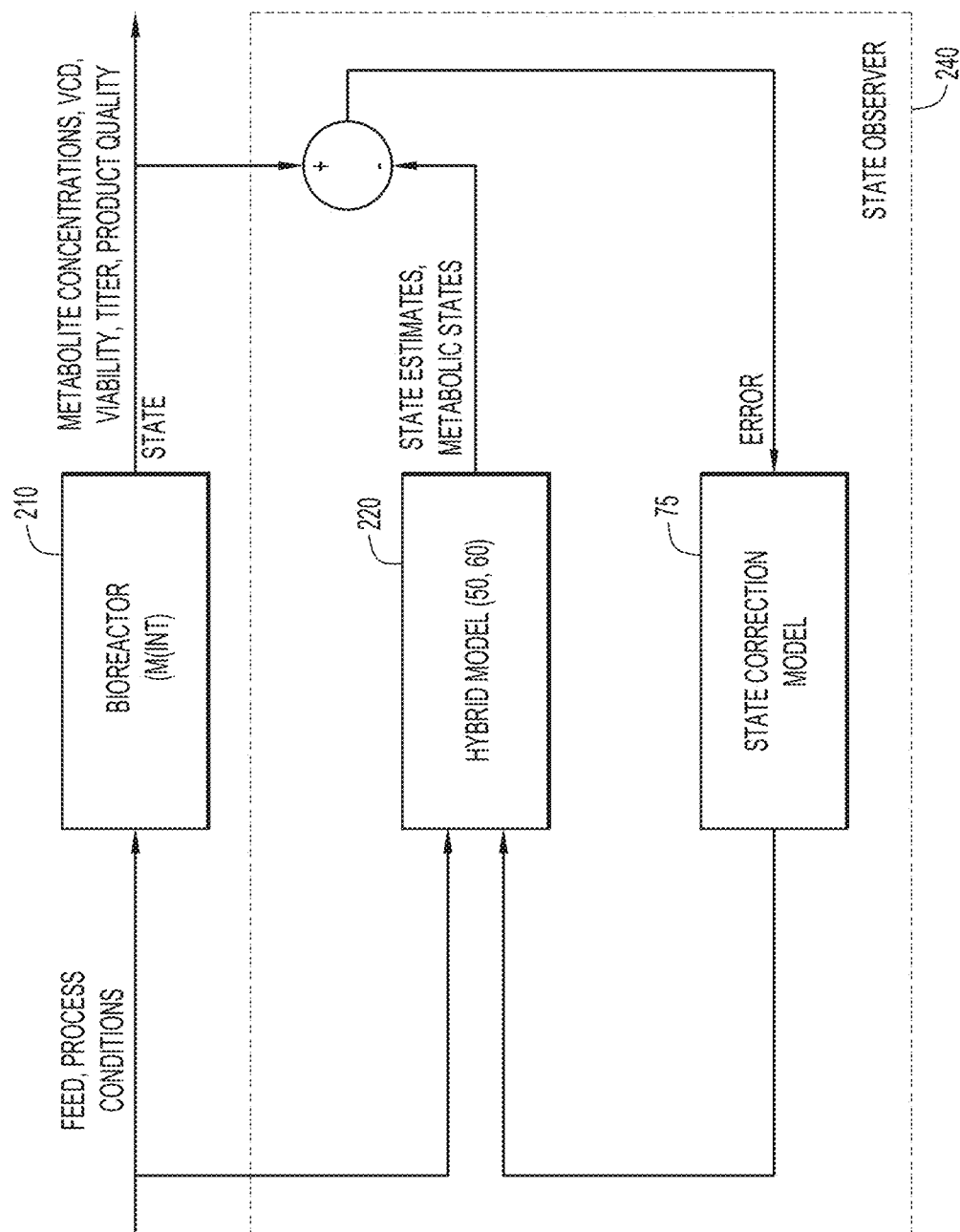
FIG. 2 shows an example illustration of a state observer with state correction, according to the present disclosure.

State correction model 75 mitigates error in the system, according to the state observer depicted in FIG. 2. The difference between the output of the hybrid model and the measured data may be determined, and provided as an error signal to state correction model 75. The state correction model acts to minimize the error, and to drive the error signal to zero as a function of time. In some aspects, state correction corresponds to techniques associated with an extended Kalman filter. In aspects, the state correction model 75 may be a separate module, or optionally, may be integrated into the kinetic growth model.

Referring back to FIG. 1, process monitoring engine 80 may interface with a plurality of sensors which measure one or more parameters associated with the bioreactor. These parameters may include temperature, oxygen levels, feed conditions, pH or other aspects of the bioprocess which may be monitored in real-time or in near real-time. These measurements may be provided to the hybrid model for simulating the bioreaction. These measurements may also be provided to the metabolic condition module 60 to monitor cell metabolism and generate state estimates.

Flagging and alerts engine 85 monitors the system for process deviations. If an output of the bioreactor deviates from its expected/predicted output, an alert is provided to the user. In some aspects, the bioprocess may be suspended by the system until the process is corrected. In other aspects, the system may compensate for the deviation (e.g., adjusting the feed or process conditions to reach a desired state (e.g., an optimal state)). Flagging and alerts engine 85 may also send notifications to a user regarding the state of the bioreactor. In other aspects, a notification may be sent to a user, when the internal metabolic state is classified into a suboptimal category Consumption rate and secretion rate module 90 determines the specific consumption rates and specific production rates of metabolites/analytes in the bioprocess reactor. The specific consumption data is used by the metabolic condition model 60. Outputs from the metabolic condition model 60 (for instance, estimation of specific productivity/specific consumption) may be provided into the kinetic growth model to predict product titer.

Controller 95 may receive feedback (e.g., output of the bioreactor) to control the bioreactor to automatically adjust the experimental process conditions to minimize deviation from optimal process conditions.

Database 30 contains various types of data for the kinetic and metabolic state observation system 5. Training data 32 corresponds to data to identify kinetic model coefficients, calculate metabolite specific consumption/production rates, and/or train the metabolic condition model 60 to classify the state of the cells into an optimal or sub-optimal state or determine estimate the amount of a production of a biomaterial such as the specific productivity.

Process conditions 34 correspond to the process conditions of the current bioprocess reaction. Process conditions 34 may also contain ideal process conditions that have been experimentally determined. These conditions may be supplied to the hybrid model (50, 60) to facilitate process monitoring of the current bioprocess operation or simulation/forecasting of the bioreactor. The output 36 is the output of kinetic and metabolic state observation system 5, and this output may be subtracted from the output of the experimental system in order to generate an error signal which is fed back into the input of the hybrid model.

Specific consumption rates and specific production rates may be calculated from experimental data measured during the bioprocess. In some aspects, the specific consumption and production rates may be determined using the following formulas:

$$\delta_{m,i}(t_k) = \left(m_{i,k} - m_{i,k+1} + \frac{mAdd_{i,k}}{V_k}\right)iVCD^{-1} \quad (12)$$

$$iVCD = (0.6\, x_{v,k} + 0.4\, x_{v,k+1})(t_{k+1} - t_k) \quad (13)$$

where $\delta_{m,i}(t_k)$ at time $(t_k)$ represents the specific consumption or production rates from time $(t_k)$ to the next sample point at time $t_{k+1}$. VCD corresponds to the viable cell density, and iVCD corresponds to the integrated VCD over a time step. To determine iVCD for a given time step, the time step $(t_{k+1}-t_k)$ is multiplied by a weighted combination of the viable cell density $x_v$ at time k and the viable cell density $x_v$ at time k+1. To determine the specific consumption or specific production rate $\delta_{m,i}(t_k)$, the inverse of the iVCD is multiplied by the difference in metabolite concentration over a time step $(m_{i,k}-m_{i,k+1})$, wherein $m_i$ corresponds to a specific type of metabolite. This difference is added to $mAdd_{(i,k)}$, which corresponds to a bolus or continuous feed addition of the metabolite i between the time interval t=k and t=k+1, which is divided by $V_k$. In this example, both k and i are non-negative integers. Further, it is assumed that the measurement of the metabolite i at t=k occurs before addition of the bolus.

Measurements of the metabolites and cell density may be obtained by process monitoring engine 80, and provided to the specific consumption and secretion rate model 90 to determine the specific consumption rate or the specific secretion rate of the metabolites. The specific consumption rate and specific secretion rate may be provided as input to the metabolic conditioning model. The specific consumption rate and specific secretion rate allow for translating measured experimental data into an amount each cell is consuming or producing for each of the metabolites. In aspects, the specific consumption rate and specific secretion rate may be provided to the metabolic condition model 60, wherein the PCA and PLS statistical model engine 65 and/or data-driven machine learning engine 70 classifies the state of the cell to determine whether the system is in an optimal or a suboptimal condition, for example, with respect to a process parameter (e.g., temperature, feed concentration, pH, etc.).

FIG. 2 shows the hybrid model in the context of state observer 240. In this illustration, feed and process conditions are shown as input to the bioreactor 210. Internal states of the bioreactor are represented as M(int). However, internal states of the bioreactor, which correspond to metabolics of individual cells in the bioreactor, cannot be directly measured. The closest measurements that may be performed relative to these internal states are measurements of the output of the bioreactor 210. Outputs include metabolite concentrations, viable cell densities (VCD), product titer, product quality, viability of cells, product quality, temperature, pH, dissolved oxygen (DO), etc. Accordingly, internal estimates determined by the hybrid model are based upon indirect measurements tied to inputs and outputs of the bioreactor (e.g., process conditions).

The output of the hybrid model (e.g., state estimates, metabolic states, etc.) is combined with the output of the bioreactor, and the difference between the measured parameters and estimated parameters are fed back through state correction model 75 into the input of the hybrid model 220. The state correction model 75 seeks to modify parameters to minimize the difference between the measured bioreactor output and the hybrid model output, to drive the error signal to zero as a function of time.

In general, state estimators may be used to estimate the internal state of a system, when the state of the system is not directly measureable. In particular, Kalman filters may be used to determine an optimal estimate of the internal system states based on indirect measurements in a noisy environment. That is, based on process conditions and kinetic models, a Kalman filter may be used to optimally estimate the internal state(s) of the system. Kalman filters are especially suitable for producing optimal estimates of system states in noisy systems. In this example, the state correction model 75 may comprise a Kalman filter or extended Kalman filter. The Kalman filter or extended Kalman Filter (EKF) may be used to determine optimal state values, wherein the error is combined with uncertainty in model state estimates, uncertainty in the state measurements, and covariance of the errors. In some aspects, the Kalman filter is applicable to the kinetic growth model.

In this example, the state observer comprises the hybrid model, which includes the kinetic growth model 50 and the metabolic condition model 60. The kinetic model tracks how many cells are present, including non-visible lysed cells (lysed cells generally have cell membranes that are not intact) and the amounts of the different metabolites. The metabolic conditioning model evaluates functional aspects of the bioreaction, (e.g., are the cells producing more target protein or are the cells outside of optimal conditions, which would cause a quality control issue in the production of the product (titer)/target). The hybrid model allows a material balance analysis to be performed (based on cells, feed, process conditions, metabolites, and titer, etc.), and to monitor/predict the amount of product the cells will produce.

Figure 3A:
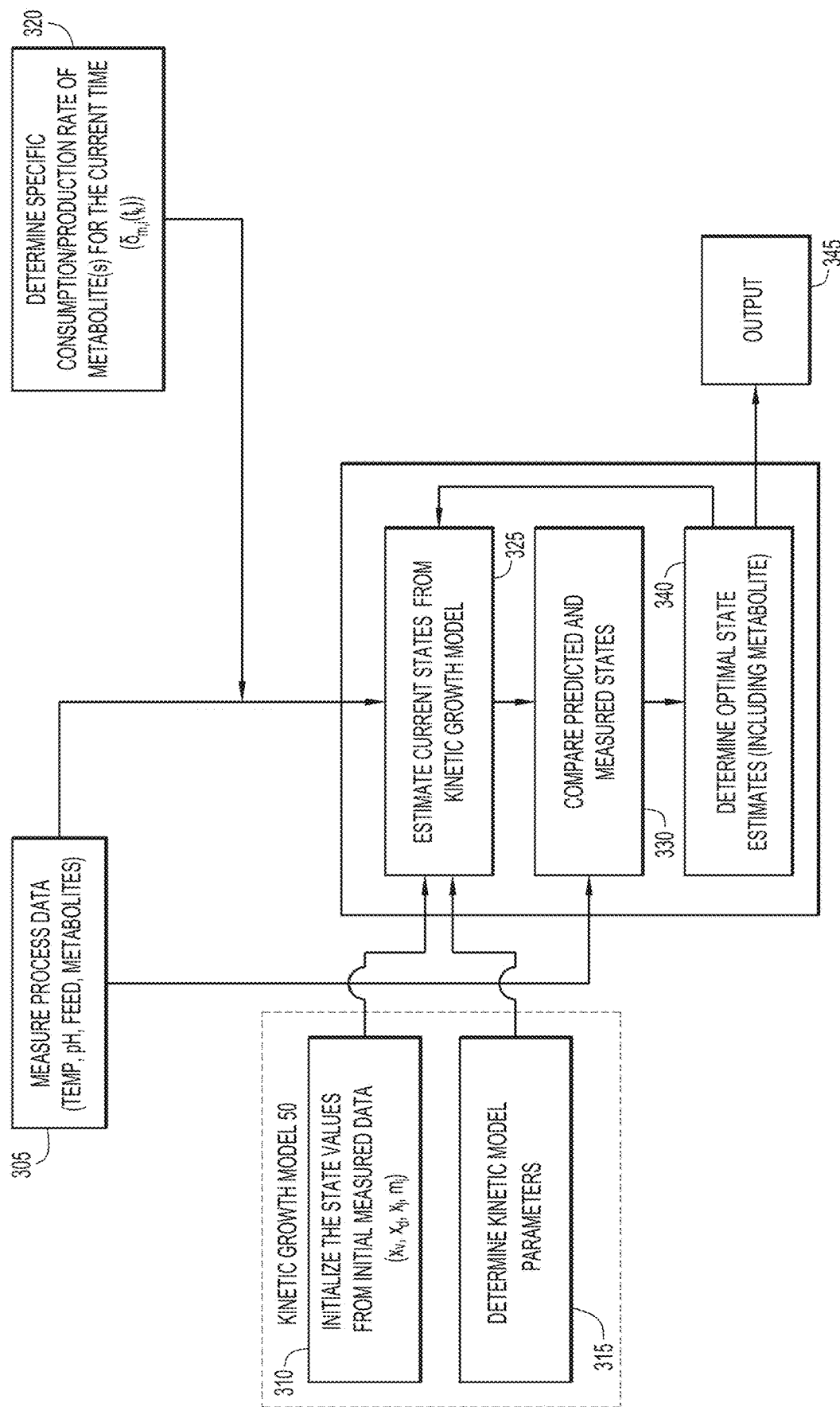
FIG. 3A shows a flowchart of a simple metabolic state observer, according to the present disclosure.
Figure 4A:
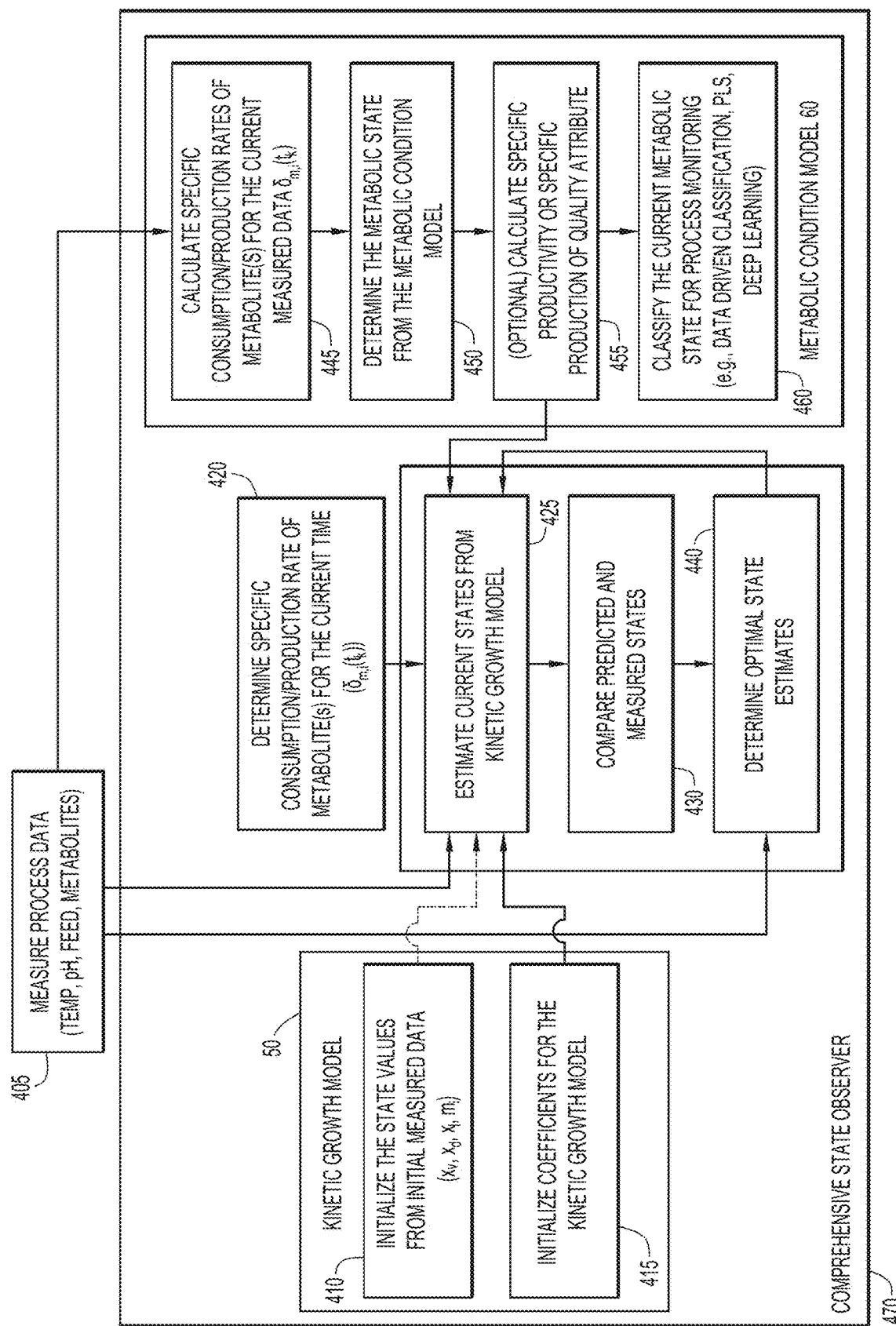
FIG. 4A shows a flowchart of a comprehensive state observer, according to the present disclosure.

FIG. 3A shows an operational flow chart of operations for a simple metabolite state observer. In this example, the simple metabolite state observer is directed to a particular metabolite of interest, rather than a set of multiple metabolites. The simple metabolite state observer includes the Monod growth model for tracking of viable cells, which consume or produce the metabolites. The simple metabolite state observer may use a lookup table to define the amount of metabolite consumed or produced for each cell for the current time point. In this example, metabolites are states in the growth model. States can be estimated for time points in which there are no corresponding measurements, to provide a state observer in between measurements of states. Unlike the comprehensive state observer shown in FIGS. 4A-4B, the simple metabolite state observer does not include the metabolic condition model 60.

In this example, the simple metabolite state observer is configured to monitor the bioreactor process as described with respect to FIGS. 1 and 2, and to estimate a future trajectory of a metabolite. In this example, an extended Kalman filter (EKF) may be used to account for noise in the bioprocess. However, any suitable estimator may be used.

At operation 305, process data is measured, including temperature, pH, feed conditions, time, metabolite concentrations, etc. These variables (e.g., pH, temperature, $O_2$, etc.) are treated as independent values. In some aspects, these values are measured and a zero-order hold is used to estimate the value over sampling intervals.

Typically, the process data may be measured as a function of time. The measured process data is provided to the kinetic growth model 50.

At operation 310, the kinetic growth model initializes the state values (e.g., metabolite values), including $x_v$, $x_d$, $x_l$, $m_i$, from initial measured values. The state observer (comprising the Monod equations) is initialized at start-up.

At operation 315, the kinetic growth model 50 determines parameters based on the Monod equations, wherein the parameters include viable cell density (VCD), cell viability (Viab), and a total number of lysed cells, etc. During operation, states are updated based on estimated versus measured values.

At operation 320, the specific consumption/production rate of the metabolite is determined. In some aspects, a lookup table, with data from previous experiments, may be used which correlates specific consumption/production rates based on current time. In other aspects, the specific consumption/production rates for the current time is estimated from experimental measurements from the bioprocess. Thus, metabolic states can be estimated for time points in which there are no corresponding measurements of the states, to provide a state observer between measurements.

At operation 325, parameters from the kinetic growth model are used to estimate current states, including current metabolite values. In some aspects, current states are estimated by integrating the set of kinetic equations (e.g., Eq. (1)-(11)) from the time at the beginning of the reaction to the current time, given the measured values of process parameters.

At operation 330, the predicted/estimated states from the state observer are compared to the measured experimental conditions. At operation 340, the optimal state estimates (metabolites) are determined. In some aspects, an embodiment of operation 340 is an extended Kalman filter. These values are fed back to operation 325. Thus, state estimates may be updated as a function of time from the feedback loop.

The output 345 of the kinetic growth model 50 may include product titer, metabolite concentration, viable cell density, and viability. Based on this, at operation 335, the simple metabolite state observer may estimate future values (e.g., trajectories) of metabolite(s) of interest ($m_{est}$).

The kinetic growth model does not reflect the internal state of the cells in the bioreactor. If the cells experience fluctuations or deviations in process conditions (e.g., changes in temperature, increases or decreases in metabolites, feed condition alterations, etc.), the cells may enter a suboptimal state, and the output (e.g., titer of a biologic under production) may be suboptimal. Thus, operations 325-335 provide a way to estimate the internal state of the cell, and to correlate output production with environmental variables to optimize production. Moreover, if the system deviates from an optimal range, a user may receive a notification, prompting the user to correct the bioprocess to return the reaction to optimal conditions. In some embodiments, the system may autocorrect feed or environmental conditions to return the system to optimal conditions. For example, by providing feedback to a controller controlling the bioreactor, the experimental process conditions may be automatically adjusted to minimize deviation from the optimal process conditions.

In this example, it is noted that the kinetic parameters do not change over time. However, in other embodiments, the specific consumption and production may change as a period of time, and therefore, may be updated.

Figure 3B:
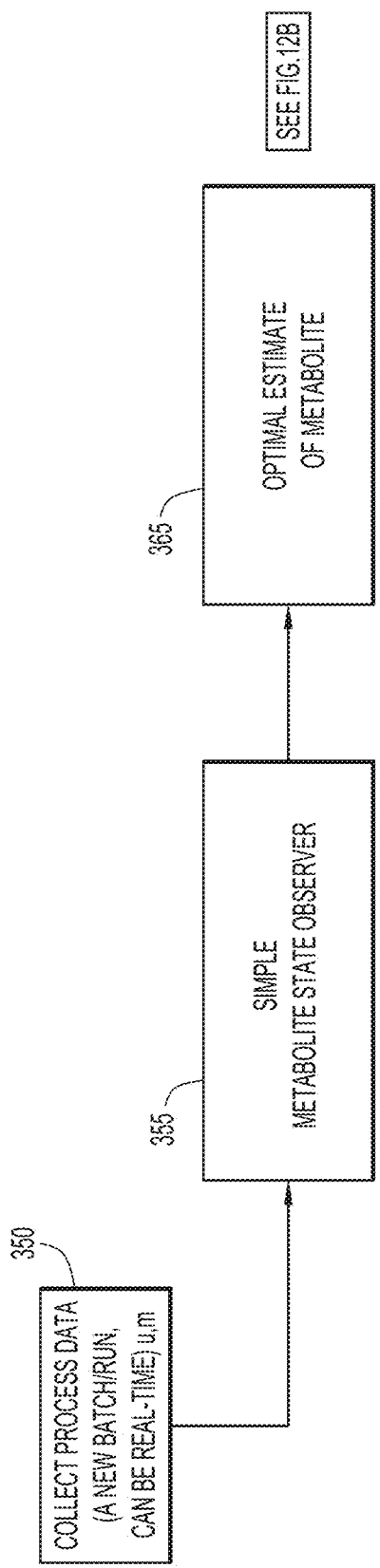
FIG. 3B shows another flowchart of a simple metabolic state observer, according to the present disclosure.

FIG. 3B shows a high level flow chart of a simple metabolite state observer, with inputs 350 being processed by the simple metabolic state observer 355 (see, FIG. 3A), to produce outputs (optimal estimates) 365.

FIG. 4 shows an operational flow chart of operations for a comprehensive state observer. In this example, the comprehensive state observer is directed to a set of multiple metabolites.

In this example, the comprehensive metabolite state observer is configured to monitor the bioreactor process as described with respect to FIGS. 1 and 2, and to estimate a future trajectory of one or more metabolites. Similar to FIG. 3A, the output of the kinetic growth model and/or the comprehensive state observer may be used to estimate future states. In this example, an extended Kalman filter (EKF) may be used to account for noise in the bioprocess. However, any suitable estimator may be used. As compared to the simple metabolic state observer, in this example, the metabolic condition model 60 is present, and the states extend to more than a single metabolite.

At operation 405, process data is measured, including temperature, pH, feed conditions, time, metabolite concentrations, etc. Typically, the process data may be measured as a function of time. The measured process data is provided to the kinetic growth model 50 and to the metabolite condition model. In other aspects, the measured process data may optionally be provided to the metabolite condition model. At operation 410, the kinetic growth model initializes the state values (e.g., metabolite values), including $x_v$, $x_d$, $x_l$, $m_i$. The state observer is initialized at start-up. During operation, states are updated based on estimated versus measured values as described below. At operation 415, the kinetic growth model 50 coefficients for the Monod equations are initialized, wherein the coefficients include $u_{max}$, $k_d$, $k_l$, $\theta_s$, $\theta_{iopt}$, $\theta_q$ and $\theta_i$.

The output of the kinetic growth model 50 (part of comprehensive state observer 470 in FIG. 4B) may include product titer, metabolite concentration, viable cell density, lysed cells and viability. Based on this, the comprehensive metabolite state observer may estimate future values (e.g., trajectories) of titer, biomaterials, viable cell density, viability, lysed cells, metabolite(s) and cell states of interest ($m_{est}$) (see, FIG. 4B).

The kinetic growth model does not reflect the internal state of the cells in the bioreactor. If the cells experience fluctuations or deviations in process conditions (e.g., changes in temperature, increases or decreases in metabolites, feed condition alterations, etc.), the cells may enter a suboptimal state, and the output (e.g., titer of a biologic under production) may be suboptimal. In a multidimensional system having a large number of states, including some states that are correlated with each other, determining which process condition(s) to adjust is challenging. Thus, metabolic condition model 60 a state and operations 425-440 provide a way to estimate the internal state of the cell, and to correlate output production with environmental conditions (variables) to optimize titer production. Moreover, if the system deviates from an optimal range, a user may receive a notification, prompting the user to correct the bioprocess to return the bioreaction to optimal conditions. In other embodiments, the system may autocorrect feed or environmental conditions to return automatically, the system to optimal conditions. This capability is described in further detail below and throughout the specification. For example, an optimization routine may be used to determine process adjustments, as described below.

At operation 420, the specific consumption/production rate of the metabolites are determined for a given time. In some aspects, a lookup table calibrated from experimental data may be used which correlates specific consumption/production rates based on current time. Thus, metabolic states can be estimated for time points in which there are no corresponding measurements of the states, to provide a state observer between measurements. In other aspects, Eqs. 12 and 13 may be used to provide consumption and production rates.

At operation 425, the Monod equations from the kinetic growth model are used to estimate current states including current metabolite values. In some aspects, current states are estimated by integrating the set of kinetic equations (e.g., Monod equations) from the time at the beginning of the reaction to the current time, given the measured values of process parameters. In other aspects, saturation kinetic equations may be used.

At operation 430, the predicted/estimated states from the state observer are compared to the measured experimental conditions. At operation 440, the optimal state estimates (metabolites) are determined. This may be performed using an extended Kalman filter. These values are fed back into the system, at operation 425. Thus, state estimates may be updated as a function of time from the feedback loop. Operations 425-440 correspond to the feedback pathway shown in FIG. 2, from the output of the hybrid model through the state correction model and to the hybrid model.

Unlike the simple state observer, the comprehensive state observer comprises additional operations, including operations 445-460, which monitor metabolic states of multivariate systems. At operation 445, the specific consumption/production rates of metabolite(s) for the current measured data $\delta_{m,i}(t_k)$ are calculated. This may be performed based on measured process data. At operation 450, the metabolic state is determined from the metabolic condition model and based on the specific consumption and production rates. At operation 455, the specific productivity or specific production of quality attribute(s) may optionally be calculated. The specific productivity (production of target protein) may be used in the kinetic growth model to estimate the product titer. At operation 460, the current metabolic state for process monitoring is classified according to data-driven methods (e.g., data driven classification, PLS, deep learning, etc.). Due to the complexity of the multivariate system having a high number of states, including states that are correlated, determining which process conditions to adjust is difficult. The data driven methods provided herein (e.g., PCA and PLS statistical modeling engine 65 and data driven machine learning engine 70) may be used to reduce the dimensionality of the system, and allow identification of conditions which impact titer. In other words, conditions which are suboptimal may be identified and adjusted to return the system to optimal productivity. Present techniques provide an improvement in the state of the art, as these techniques provide granular and specific control over the bioreactor, by identification of process variables that are outside an optimally determined range. In this case, optimal refers to a range for a process or feed condition that corresponds to optimized production of titer.

For this example, it is noted that the kinetic parameters do not change over time. However the specific consumption and production may change as a period of time, and therefore, may be updated.

Figure 4B:
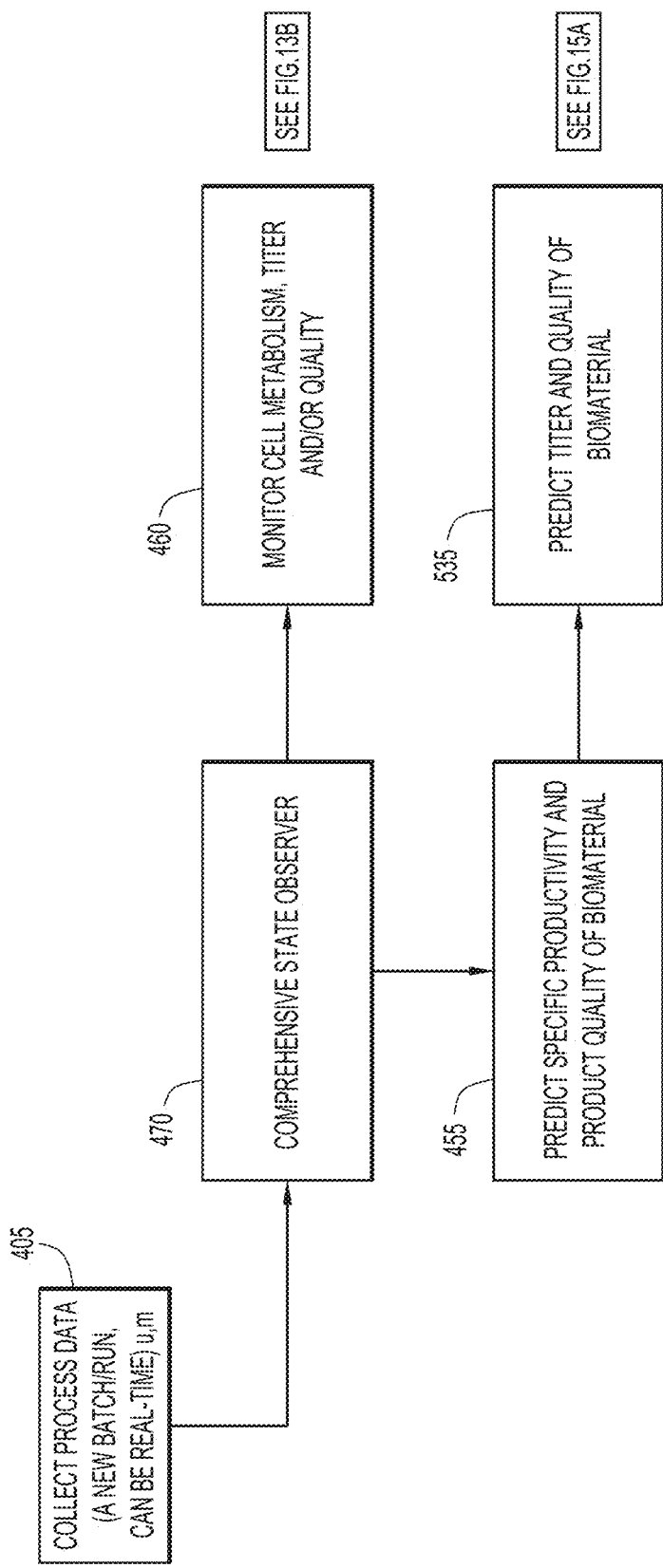
FIG. 4B shows a flowchart of inputs and outputs of a comprehensive state observer, according to the present disclosure.

FIG. 4B shows the comprehensive state observer at a high level, displaying the various outputs and the inputs of the comprehensive state observer. In particular, process data is collected at operation 405 and provided to the comprehensive state observer 470. The comprehensive state observer uses the hybrid model as described herein to monitor cell metabolism, titer, and quality at operation 460, and to predict specific productivity and product quality of the biomaterial at operation 455. The titer and quality of the biomaterial may be predicted at operation 535.

Figure 5:
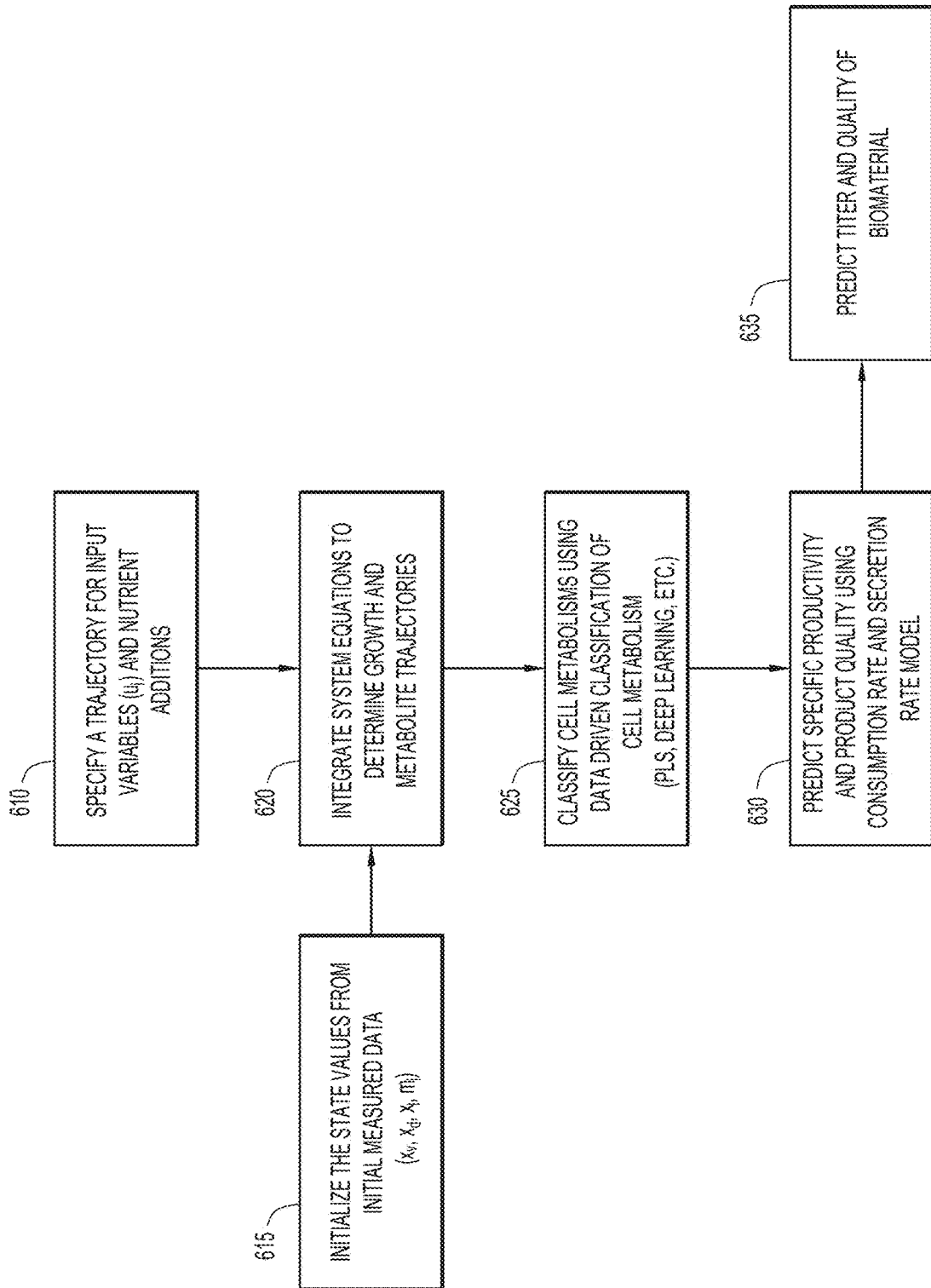
FIG. 5 shows a flowchart of operations for digital twin simulation using the hybrid model, according to the present disclosure.

As shown in FIG. 5, the hybrid model may be used in other applications. For example, the hybrid model may be used as part of a digital twin simulation, which digitally replicates behavior of living systems.

Optimization involves searching through various input variables to find a set that maximize titer, quality or other desired result using an optimization package. Input variables typically include nutrient additions and independent process parameters such as temperature and pH. The optimized parameters may be provided as input variables to operation 610.

At operation 610, a trajectory is specified for input variables ($u_i$) and nutrient additions. At operation 615, the state values are initialized from initial measured data ($x_v$, $x_d$, $x_l$, $m_i$). At operation 620, the specified trajectories of operations 610 and the initialized state values of operation 615 are received as input. The Monod growth equations to determine growth and metabolite trajectories are integrated over suitable parameter ranges.

At operation 625, cell metabolism is classified using data-driven classification (e.g., PLS, deep learning, etc.). At operation 630, specific productivity and product quality are predicted using the hybrid model, comprising kinetic growth module 50 and metabolic condition module 60. At operation 635, titer and quality of biomaterial is predicted. In this example, the hybrid model is configured to mirror or replicate outputs produced by the bioreactor.

Figure 6:
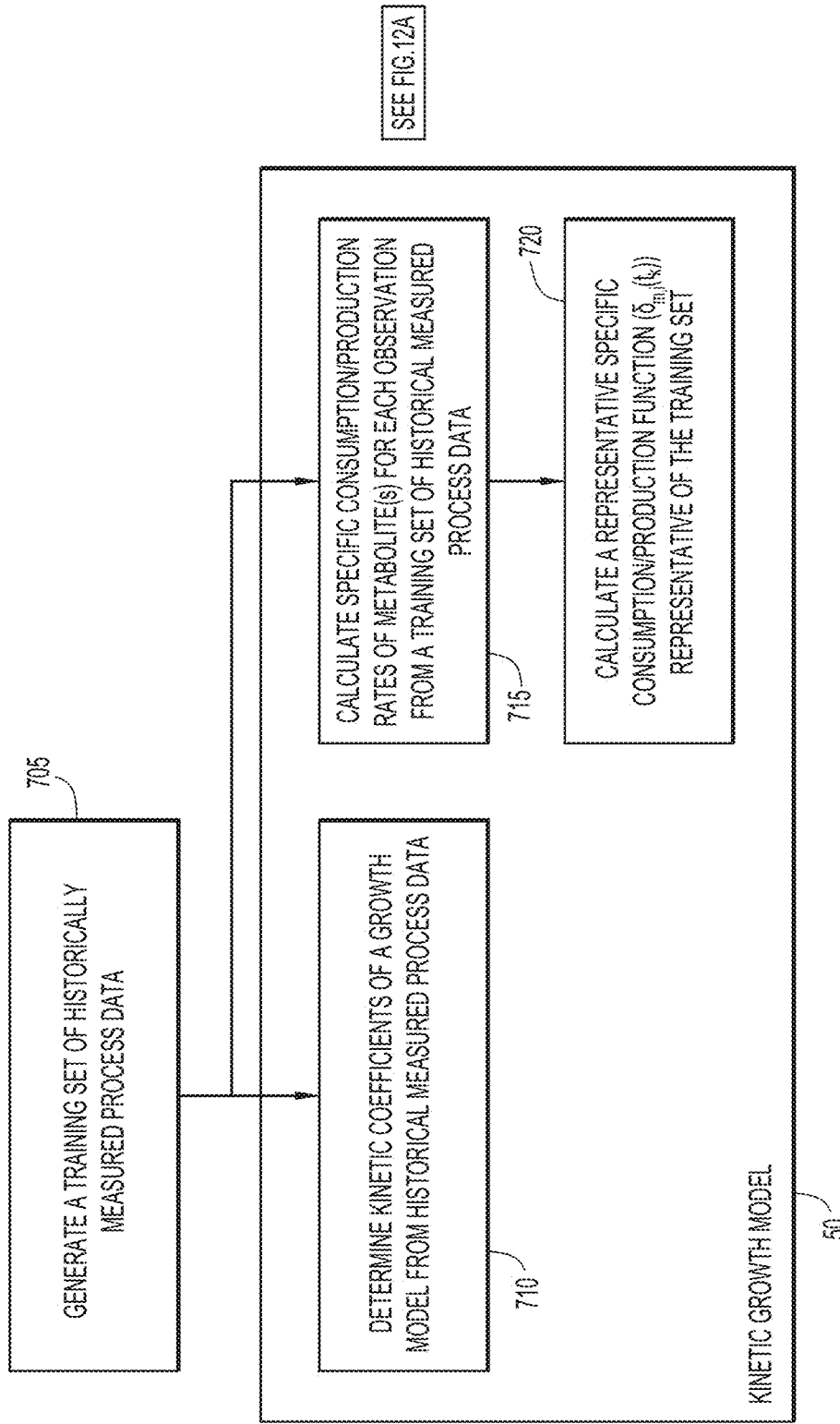
FIG. 6 shows a flowchart of calibration of the kinetic growth model according to the present disclosure.

FIG. 6 shows an example calibration of the kinetic growth model 50. At operation 705, a training set of historically measured process data is generated.

At operation 715, specific consumption/production rates of metabolite(s) are calculated for each observation from a training set of historical measured process data. At operation 720, a representative specific consumption/production function ($\delta_{m,i}(t_k)$) is calculated representative of the training set. In this example, a lookup table is used to perform this function. In some aspects, there is a separate function (lookup table) for each metabolite. In general, any suitable approach may be used to estimate specific consumption/production at a given time.

Figure 7:
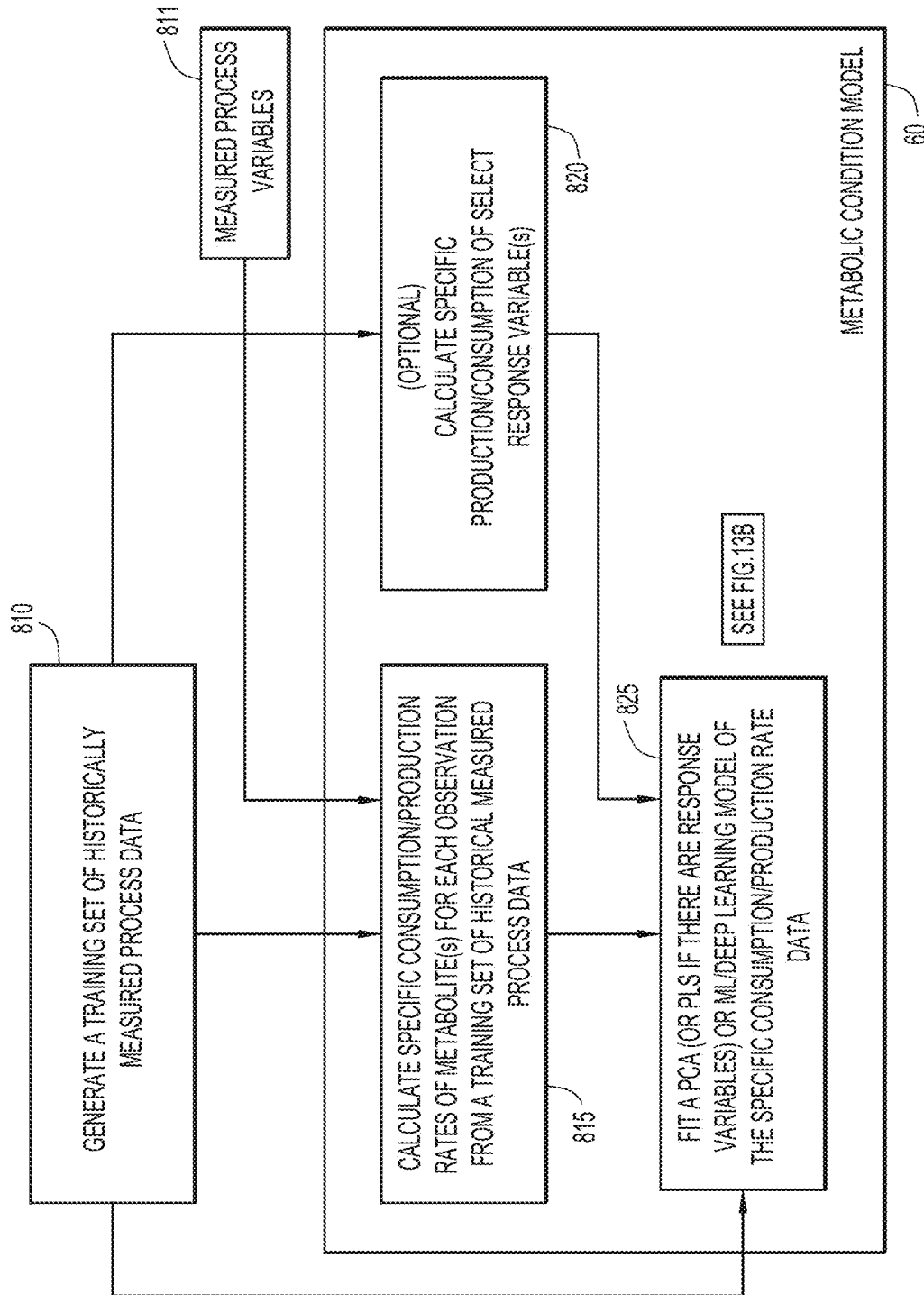
FIG. 7 shows a flowchart of calibration of the metabolic conditioning model according to the present disclosure.

FIG. 7 shows an example calibration method for the metabolic condition model 60. At operation 810, a training set of historically measured process data is generated. Optionally, measured process variables 811 may be added to the metabolic condition model. At operation 815, specific consumption/production rates of metabolite(s) are calculated for each observation from a training set of historical measured process data.

At operation 820, specific consumption/production rates of metabolite(s) are calculated for select response variables. Response variables include titer (yield) and quality metrics. This operation is optional.

At operation 825, a PCA (or PLS if there are response variables) is fit to the specific consumption/production rate data. The metabolic conditioning model may contain measured process parameters in addition to the specific consumption/production rate data.

Figure 8:
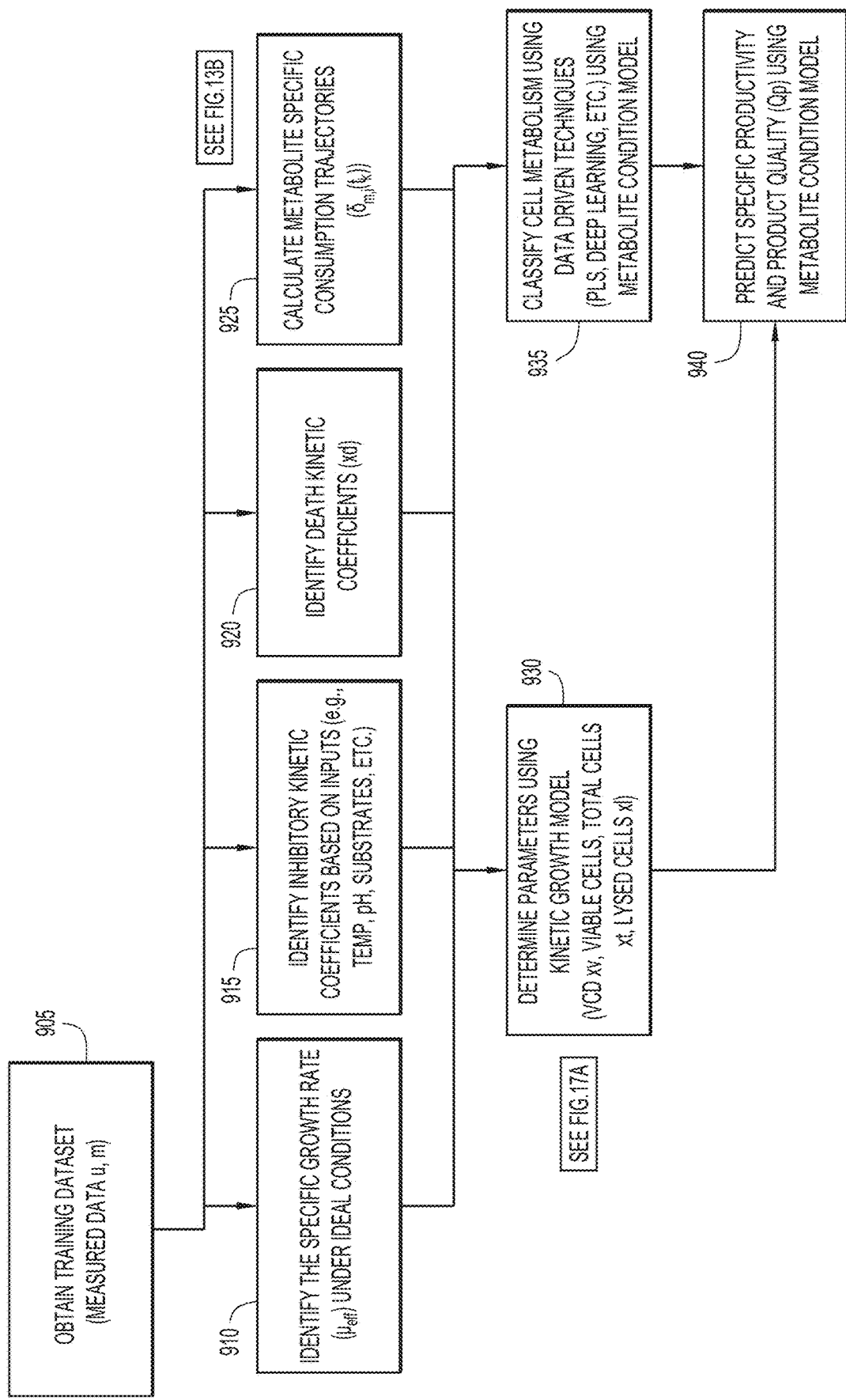
FIG. 8 shows a flowchart of calibration of the hybrid model according to the present disclosure.

FIG. 8 is a flowchart of operations of hybrid model calibration (decoupled system identification), including both the kinetic model and the metabolic conditioning model. Operations 910, 915 and 920 correspond to the kinetic growth model. Operation 925 corresponds to the metabolic condition model.

At operation 905, a training dataset is obtained. At operation 910, the specific growth rate is identified, under ideal conditions. At operation 915, inhibitory kinetic coefficients are identified. At operation 920, death kinetic coefficients are identified. At operation 925, metabolite specific consumption trajectories are calculated. These values may be provided to the kinetic growth model to determine various parameters (e.g., VCD, viable cells, total cells, lysed cells, etc.) at operation 930. At operation 935, cell metabolism is classified using data-driven techniques using the metabolite condition model 60. At operation 940, specific productivity and product quality may be predicted using the cell metabolic condition model.

Figure 9A:
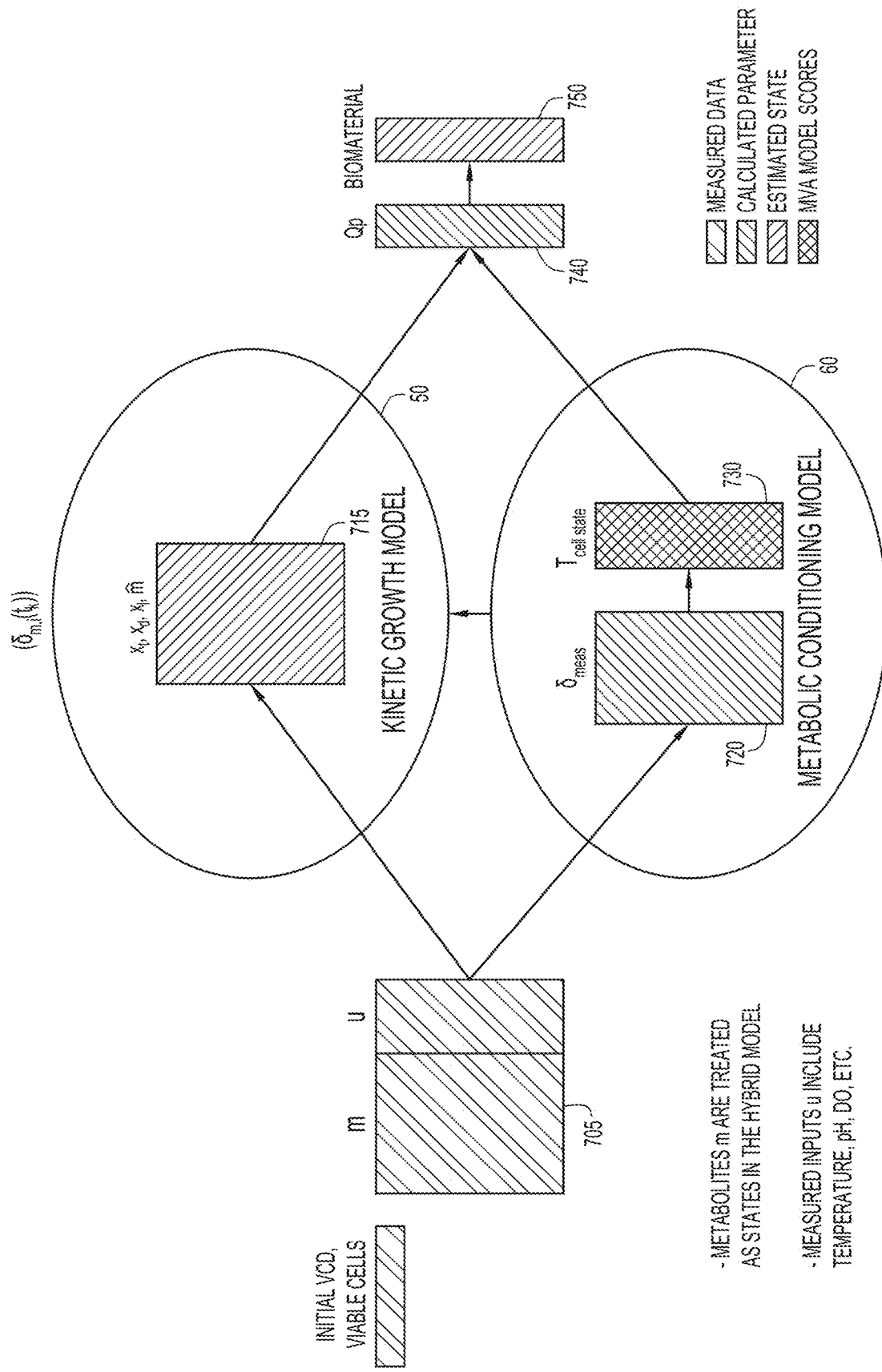
FIG. 9A shows a data flow pathway through the hybrid model according to the present disclosure.

FIG. 9A is an example of data flow through the hybrid model. Data component 705 corresponds to process measurements for the bioreactor (m, u). The experimental data is provided to the kinetic growth model, to generate estimated growth states 715 ($x_t$, $x_d$, $x_l$, $\hat{m}$), where $\hat{m}$ is a state estimate, and to the metabolic conditioning model 60 to generate calculated parameters 720 ($\delta_{meas}$) and metabolic cell states 730. The upper portion of the figure corresponds to the kinetic growth model, and the lower portion of the figure corresponds to the metabolic conditioning model. Although not shown in this figure for simplicity, data from the lower path may be provided to the upper path, as described herein.

Cell states 730 are generated based on the calculated parameters 720. From these sets of data (715 and 730), calculated parameters for product titer 740 Qp and biomaterial 750 are determined.

These examples are not intended to be limiting with regard to data flow through the hybrid model, as additional data flow pathways may be described in the application. Additional pathways for data flow may apply to the hybrid model.

Figure 9B:
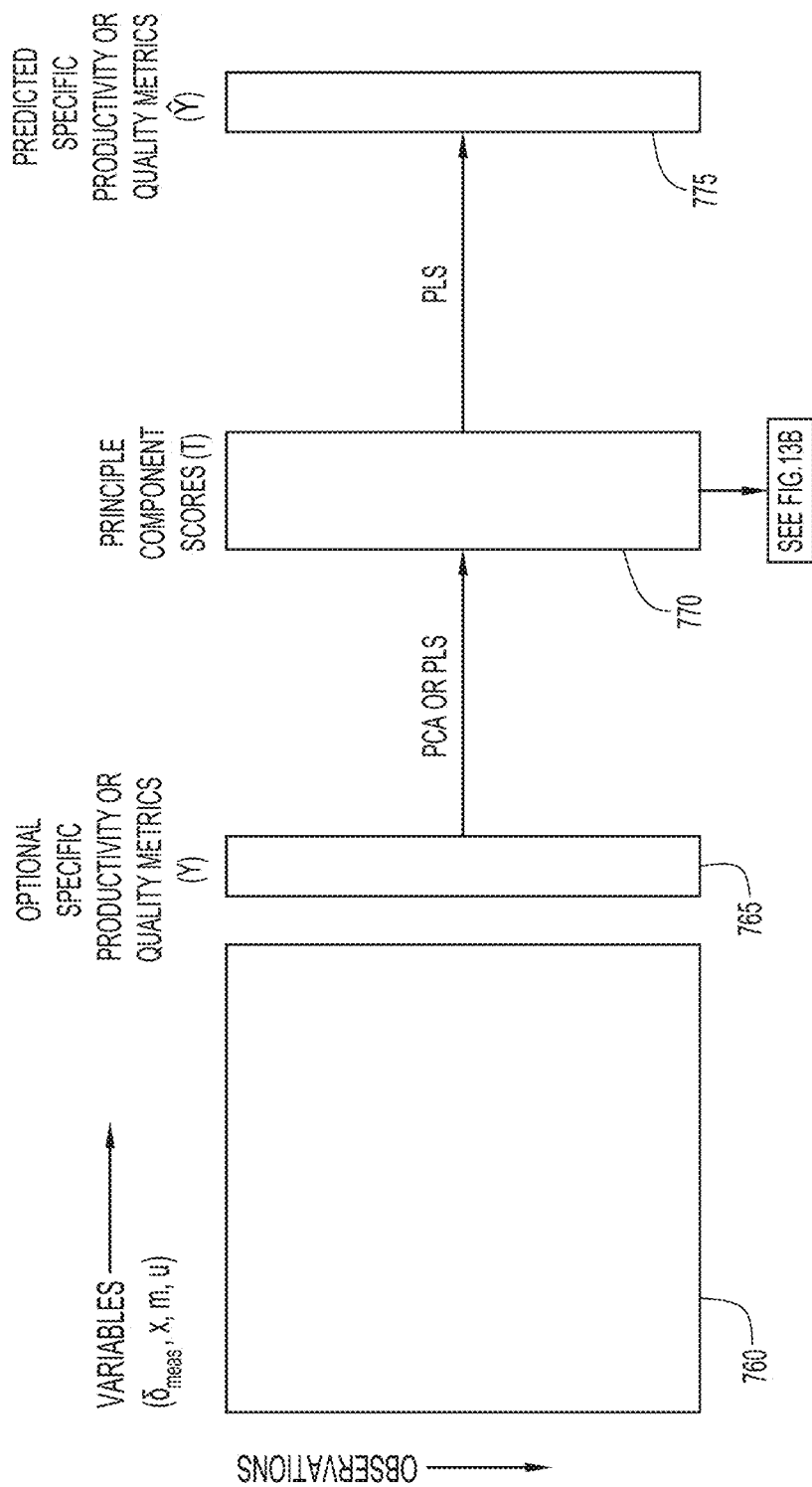
FIG. 9B shows a data flow pathway for PCA/PLS for a metabolic condition model, according to the present disclosure.

FIG. 9B shows a data flow pathway for PCA/PLS for the metabolic condition model. Optionally, variables 760 are used to determine specific productivity or quality metrics 765. Variables 760 and productivity/metrics 765 are used for PCA or PLS analysis to generate principle component scores (T) and/or to generate predicted specific productivity or quality metrics 775.

FIG. 10 is a table showing various bioreactor runs and the conditions used for each run. As can be seen from this chart, process conditions (e.g., pH, temperature, feed, etc.) are varied to find optimized conditions to produce optimized titer. The process conditions may be adjusted based on an optimization method to determine a set of process conditions that optimize predicted trajectories, product quantity (titer), and/or product quality.

Finding the optimal adjustments or settings for a process may be defined as finding the set of manipulated variables (u or independent variables, in this case, process conditions and feeds) that minimize a mathematical objective function j.

$$\min_{u|_{[t]}} j \qquad (14)$$

For example, an objective function to maximize the titer at a future time point $t|_{[t+k]}$ may take the following form:

$$j = -\widehat{IgG}|_{[t+k]}, \text{ where } \widehat{IgG}|_{[t+k]} = f_{IgG}(x|_{[t]}, u|_{[t]}), \qquad (15)$$

wherein $\widehat{IgG}|_{[t+k]}$ is the predicted titer at the future time point, $x|_{[t]}$ are the current value of the states, and $u|_{[t]}$ are the set of manipulated variables to be implemented between now [t] and the future time point [t+k].

There may be multiple objectives that are to be simultaneously optimized. This may be performed by weighting the objectives based on their importance. For example, to maximize titer and maintain a quality metric on target, the objective function may take the following form:

$$j = -\theta_{IgG}\widehat{IgG}|_{[t+k]} + \theta_q(\hat{q}|_{[t+k]} - q_{sp})^2, \qquad (16)$$

wherein $\theta$ are the relative weights for each parameter to be optimized, and $q_{sp}$ is the target or setpoint for the quality parameter q.

There is a similar function ($f_q$) to the function for IgG to predict the future quality variable at a future time point.

Often, there are constraints added to the function. For example, the optimization objective to maximize titer subject to maintaining quality within operating specifications may be governed by the following equation:

$$j = -\theta_{IgG}\widehat{IgG}|_{[t+k]} + \theta_q(\hat{q}|_{[t+k]} - q_{sp})^2, \qquad (17)$$

subject to $$q_{min} \leq \hat{q}|_{[t+k]} \leq q_{max}. \qquad (18)$$

In order to prevent the optimization algorithm from selecting a new set of inputs that are infeasible, limits are also placed on u. The aggressiveness of the control action is tuned by placing penalties on changes in u from recipe or current settings. This prevents the controller from making erratic or large changes to the process conditions that provide minimal improvement to the objective parameters. The complete objective function then is described as finding the optimal set of feasible u that maximizes titer (IgG) and maintains quality on target and within specified limits. This may be governed by the following equations:

$$j = -\theta_{IgG}\widehat{IgG}|_{[t+k]} + \theta_q(\hat{q}|_{[t+k]} - q_{sp})^2 + \theta_u(u|_{[t]} - u_{sp})^2 \qquad (19)$$

subject to $$q_{min} \leq \hat{q}|_{[t+k]} \leq q_{max}, \qquad (20)$$

$$u_{min} \leq u|_{[t]} u_{max}, \qquad (21)$$

wherein $\theta_u$ are the penalty weights for u (note there may be more than one u), and $u_{sp}$ is the target value of u, which is usually a setpoint value or the current value.

EXAMPLES

Figure 11:
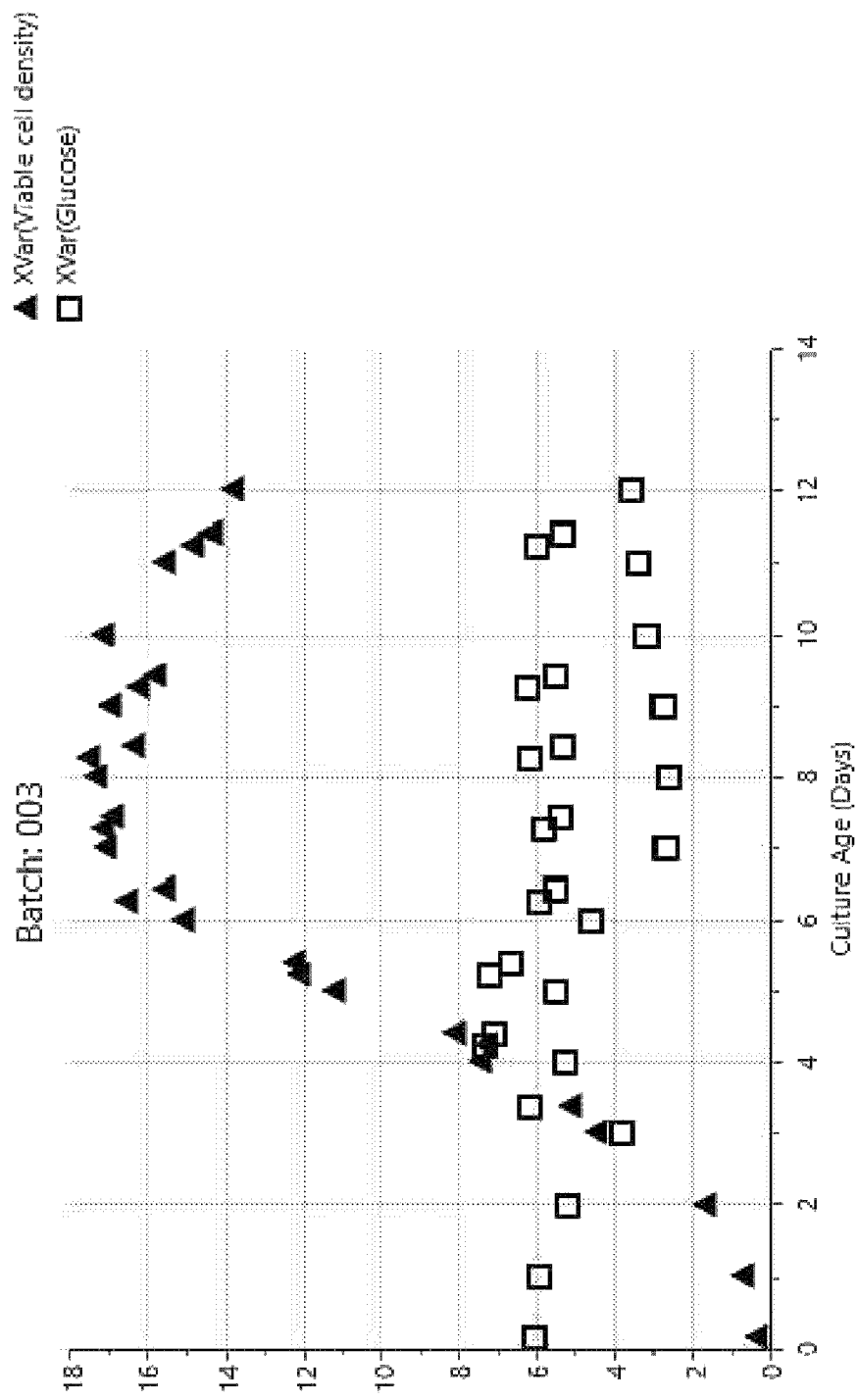
FIG. 11 shows measured trajectories (e.g., center point) for glucose concentration and viable cell density for typical experimental data according to the present disclosure.

FIG. 11 shows example trajectories for VDC and glucose. This data may be used to determine center points for these respective parameters.

Figure 12A:
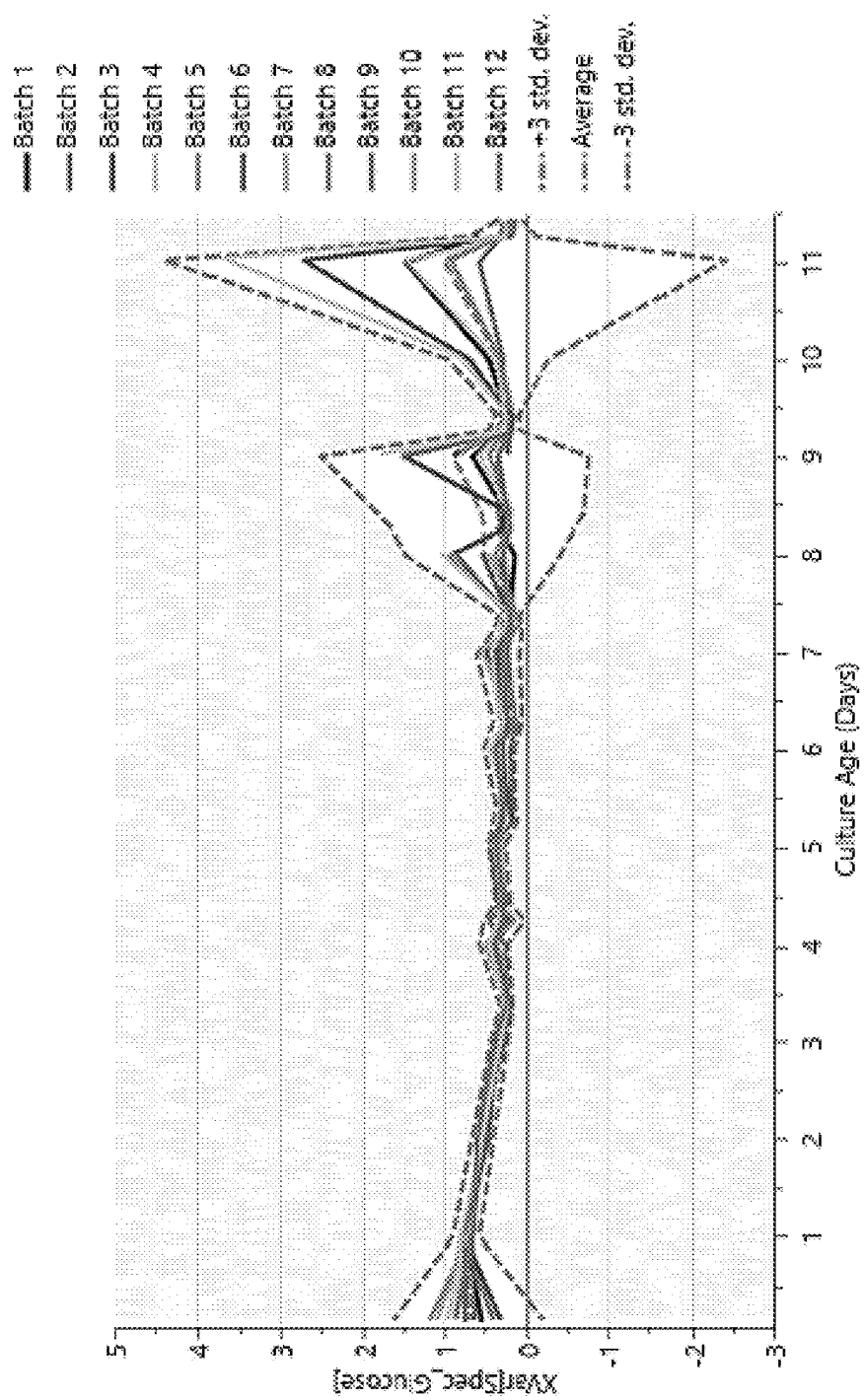
FIG. 12A shows an example of calculated specific consumption rates for a metabolite (e.g., glucose) from experimental data, according to the present disclosure.
Figure 12B:
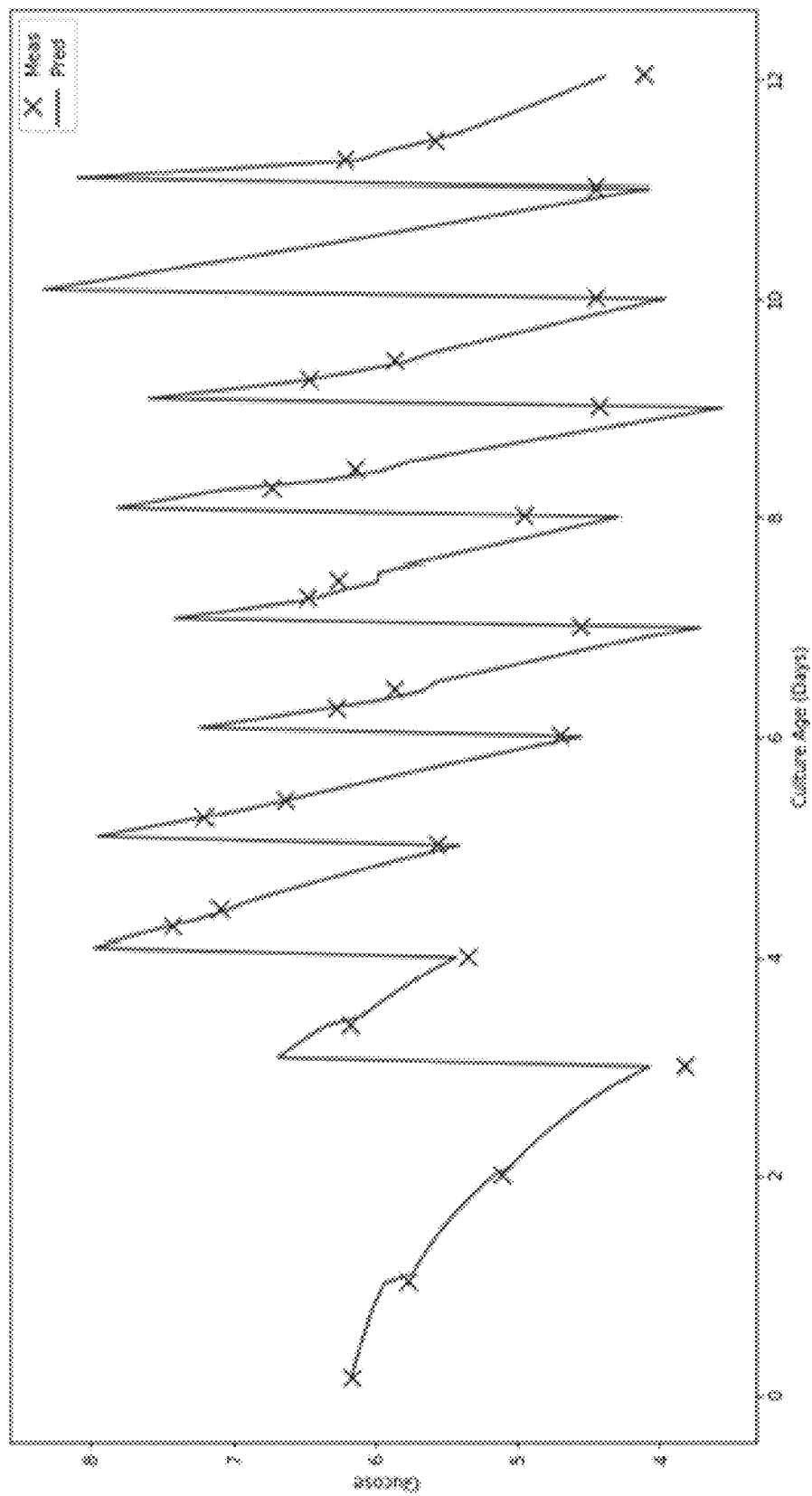
FIG. 12B shows the output of a state observer for a metabolite (e.g., glucose) comparing the predicted metabolite state versus the measured values, according to the present disclosure. In this example, the predicted state (estimate) of the metabolic state observer correlates with the experimentally measured value.

FIGS. 12A-12B show examples of metabolite state estimation, e.g., for glucose. State observers for metabolites may be built using the following procedure.

1. Calculate the specific consumption/secretion rates from the data collected.

Note that $\delta_{m,i}(t)$ at time (t) represents the consumption rate from (t) to the next BEM sample point. The following equations may be used:

$$\delta_{m,i}(t_k) = \left(m_{i,k} - m_{i,k+1} + \frac{mAdd_{i,k}}{V_k}\right) iVCD^{-1} \quad (12)$$

$$iVCD = \left(\frac{2}{3} x_{v,k} + \frac{1}{3} x_{v,k+1}\right)(t_{k+1} - t_k) \quad (13)$$

wherein $mAdd_{i,k}$ is the bolus addition of the metabolite at t=k. It is assumed that the measurement of the metabolite at t=k is before the addition of bolus.

2. Calculate the average trajectory from the training set. Use of the SIMCA average BEM trajectory is a simple way to determine $\delta_{m,i}(t)$.
3. For simulation and state observation, the parameter $\delta_{m,i}(t)$ is calculated using a zero order hold on the BEM values.

Figure 13A:
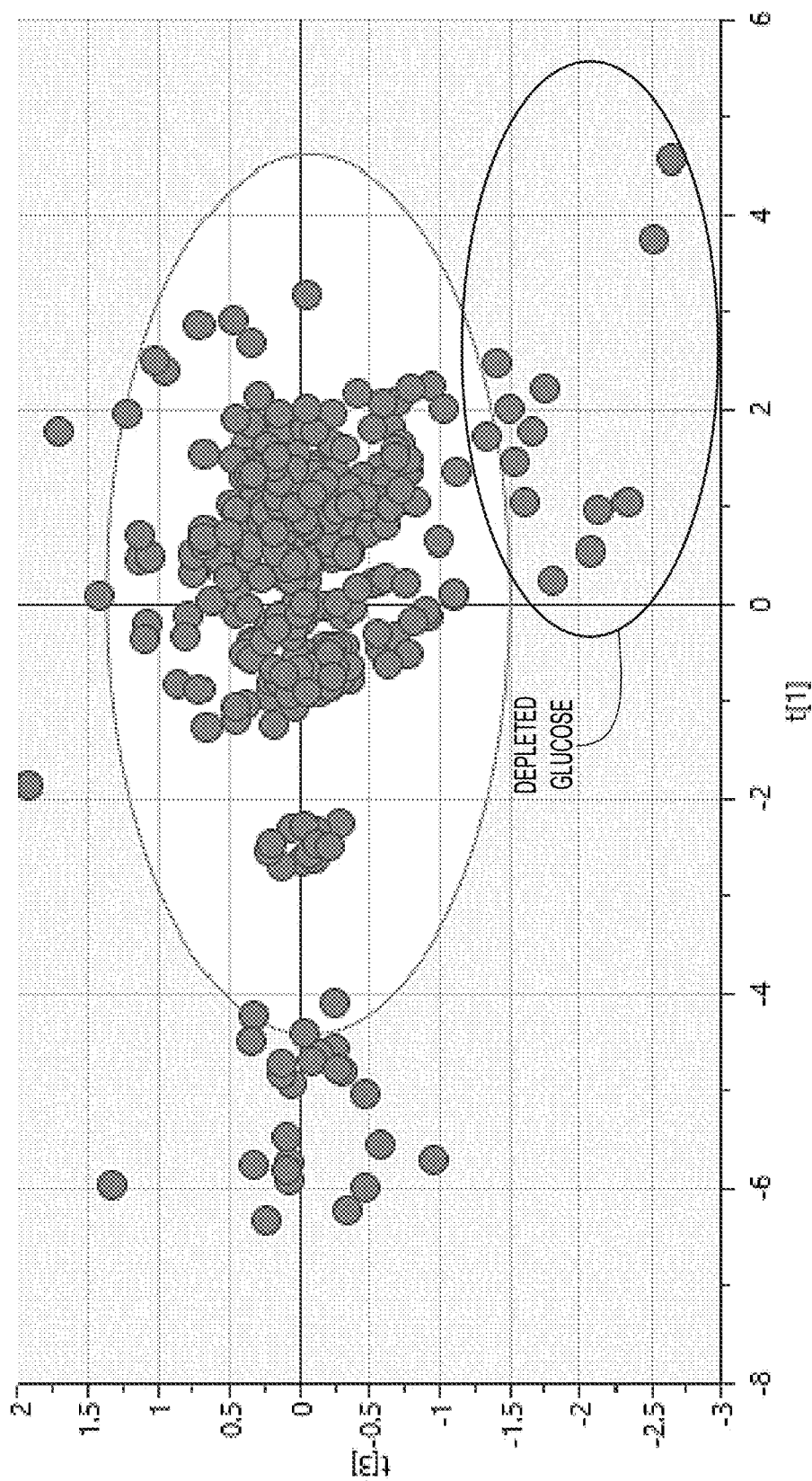
FIGS. 13A-13C show example outputs of a cell state classification by the hybrid model, according to the present disclosure.
Figure 13B:
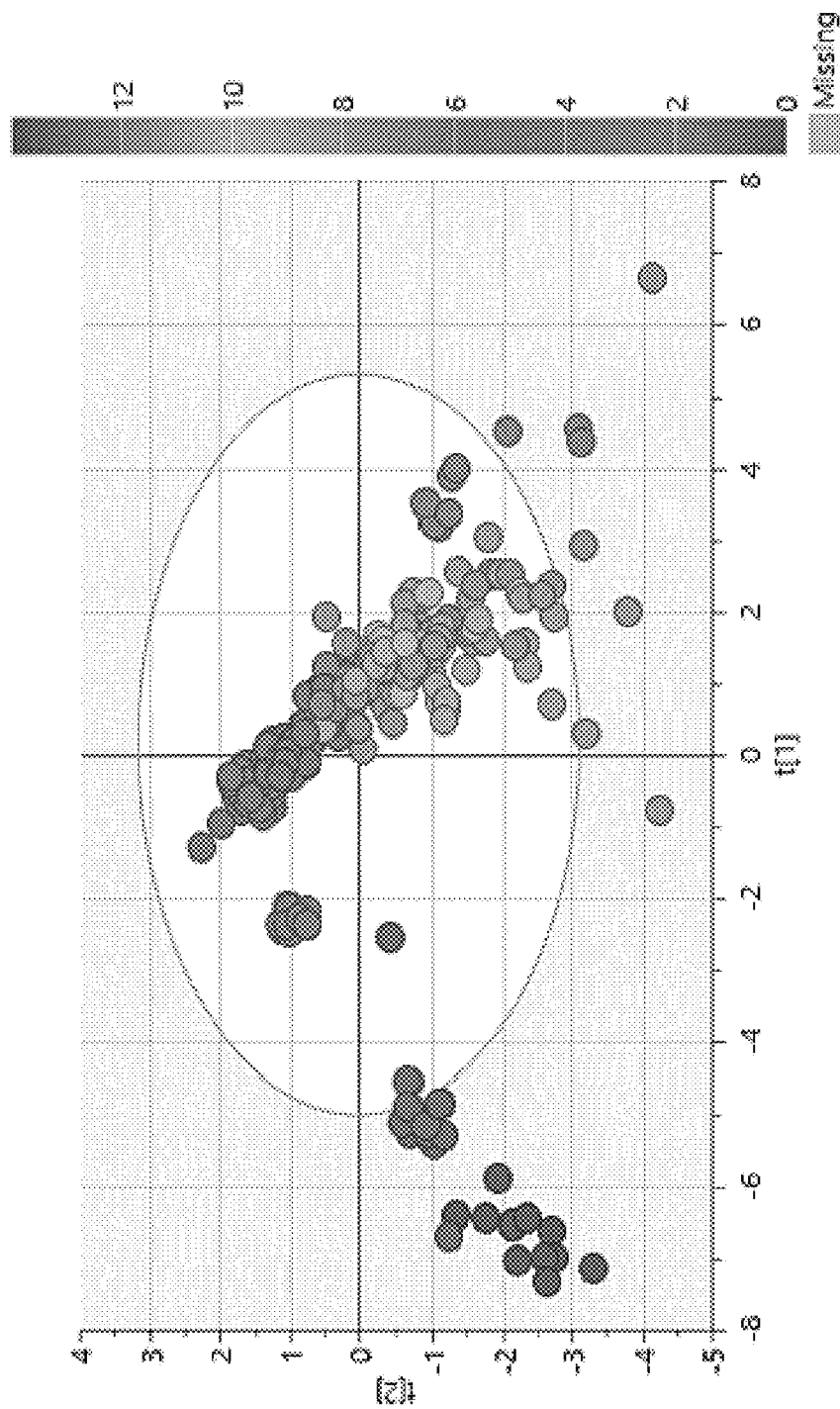
Figure 13C:
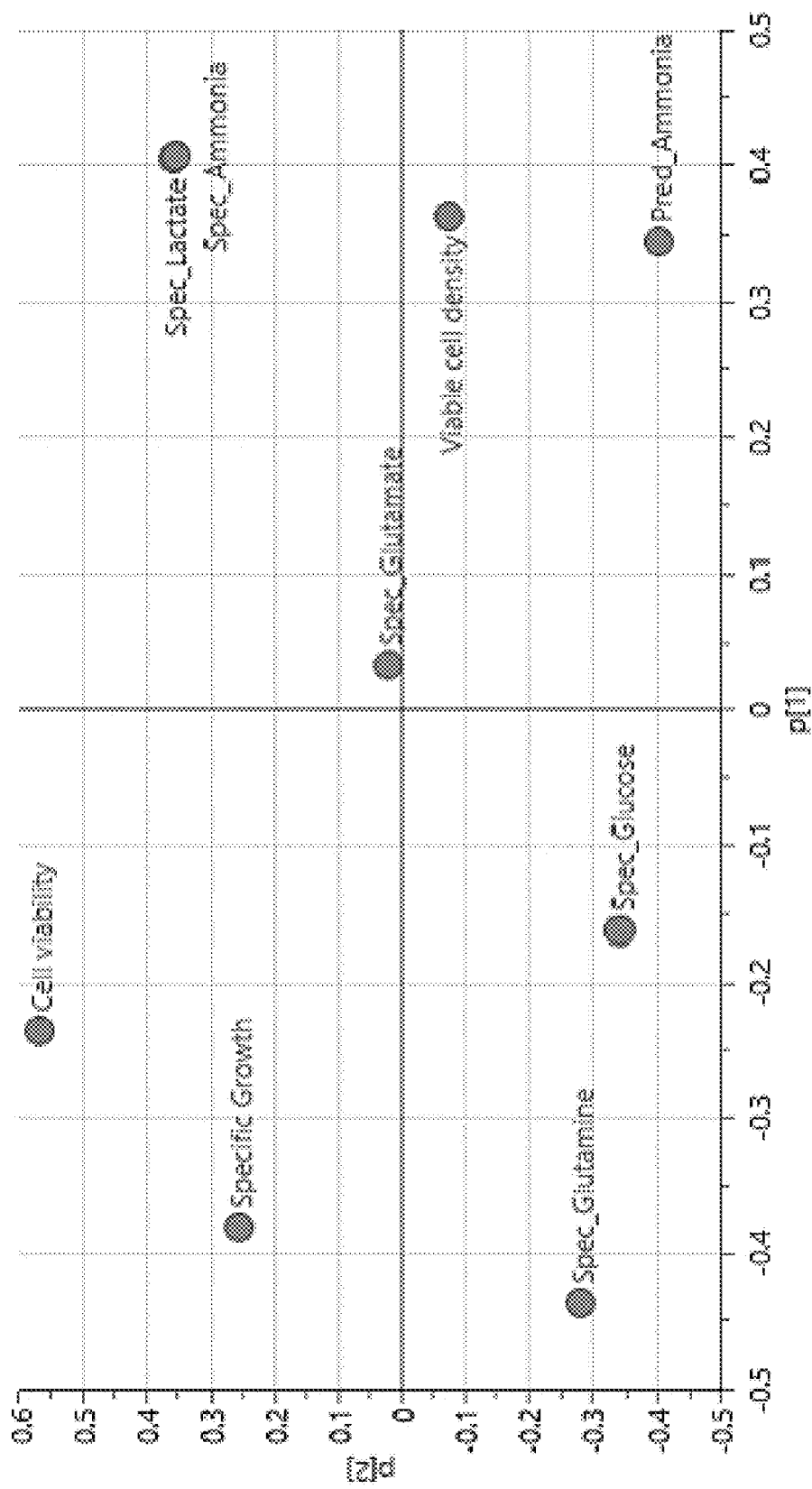

FIGS. 13A-13C show examples of cell state classification using a data-driven approach. In this approach, specific consumption rates are calculated based on the measured data, e.g., using the methods as described herein, to calculate $\delta_{m,i}(t_k)$. The set of $\delta_{m,i}(t_k)$ values may be used to construct a data-driven model to classify the cell state (e.g., metabolites).

In some aspects, cell state classification is performed using the metabolic condition model to estimate specific consumption rates or specific production rates for the metabolite. In some aspects, a machine learning process may be used to classify cell state. In other aspects, a statistical model may be used to classify the cell state. For example, PCA may be used to classify the system at a high level, for example, to determine whether the cell culture growth is operating in an optimal range (see, FIG. 13B). PLS may be used to classify individual metabolites, for example, to predict titer and/or product quality and to determine whether individual parameters are operating within an optimal range (see, FIG. 13A, for glucose). FIG. 13C shows state observation predictions for various parameters (e.g., growth, viability, byproducts such as ammonia, amino acids, feed, etc.).

Figure 14A:
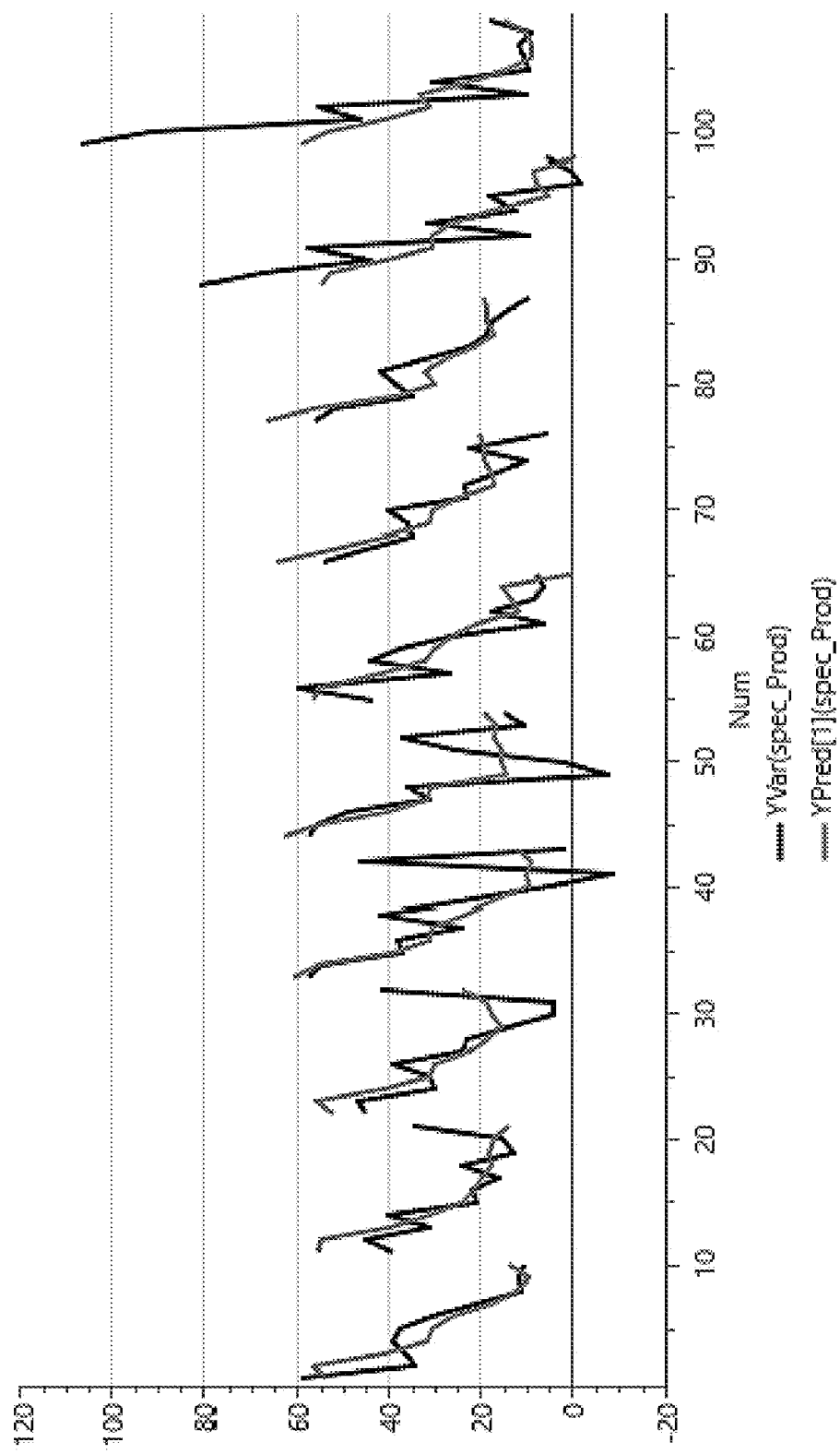
FIGS. 14A-14C show examples of productivity and product quality as predicted by the hybrid model, according to the present disclosure.
Figure 14B:
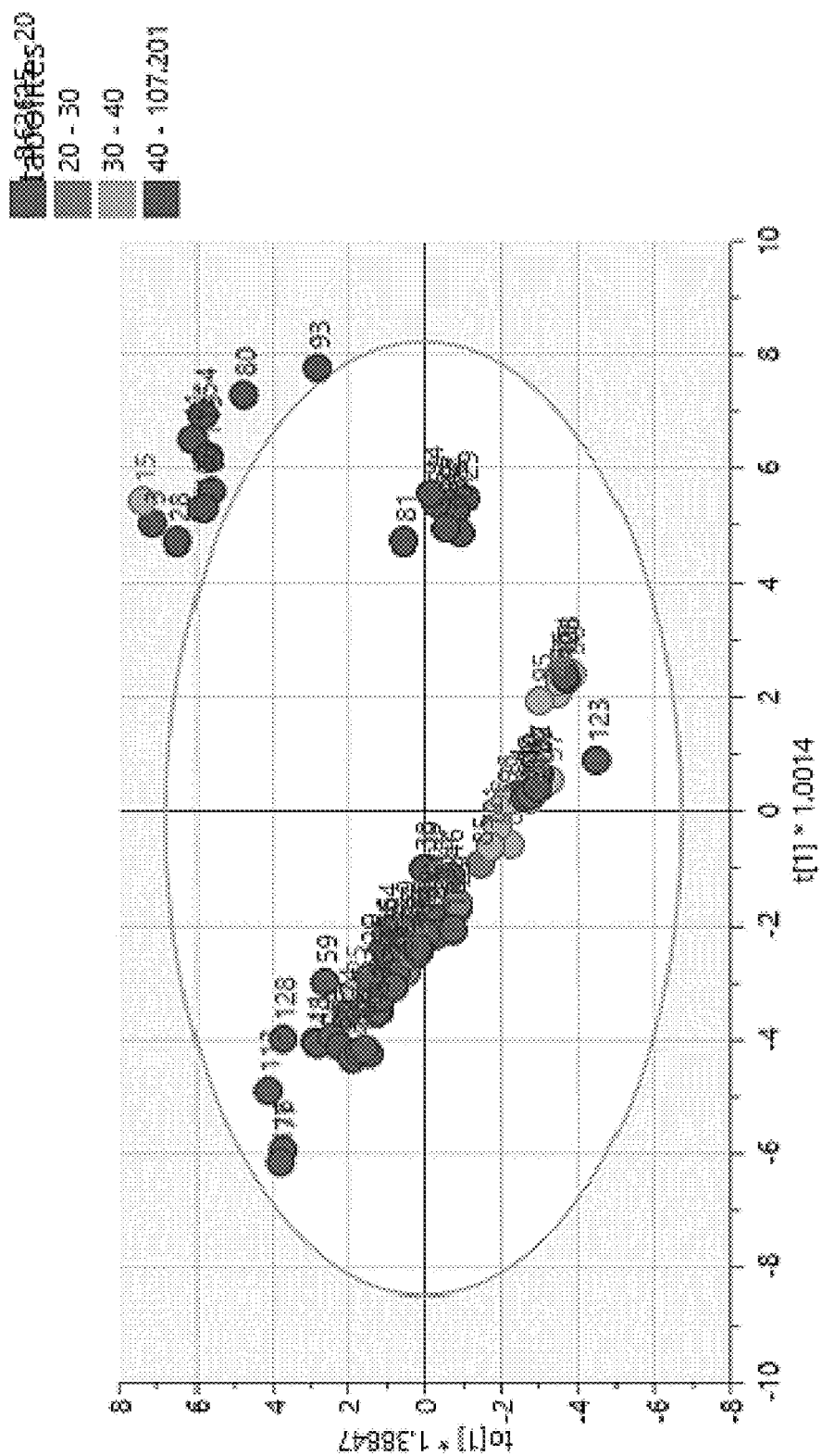
Figure 14C:
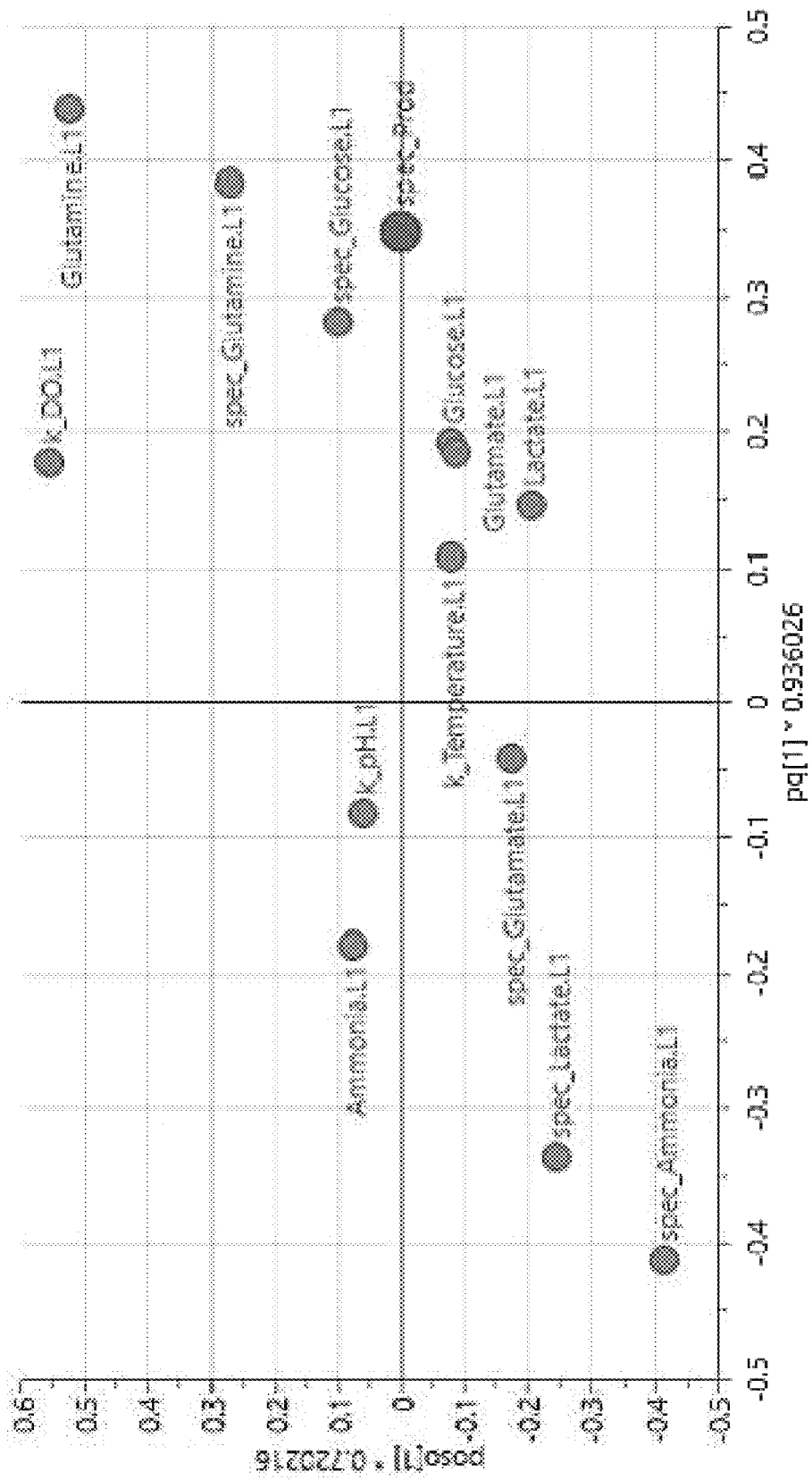

FIGS. 14A-14B show identification of parameters that correlation to productivity. Relationships that are correlational (not necessarily causal) may provide valuable insight into managing bioprocess reactions. FIG. 14C shows that ammonia decreases productivity, and all other metabolites increase productivity. Consumption of nutrients (e.g., glucose, glutamine, etc.) are related to high productivity. Lower consumption (or production) of other metabolites, such as lactate and ammonia, are related to low productivity. pH and temperature shifts may also be investigated. In general, lowering pH increases productivity and lowering temperature decreases productivity.

Figure 15A:
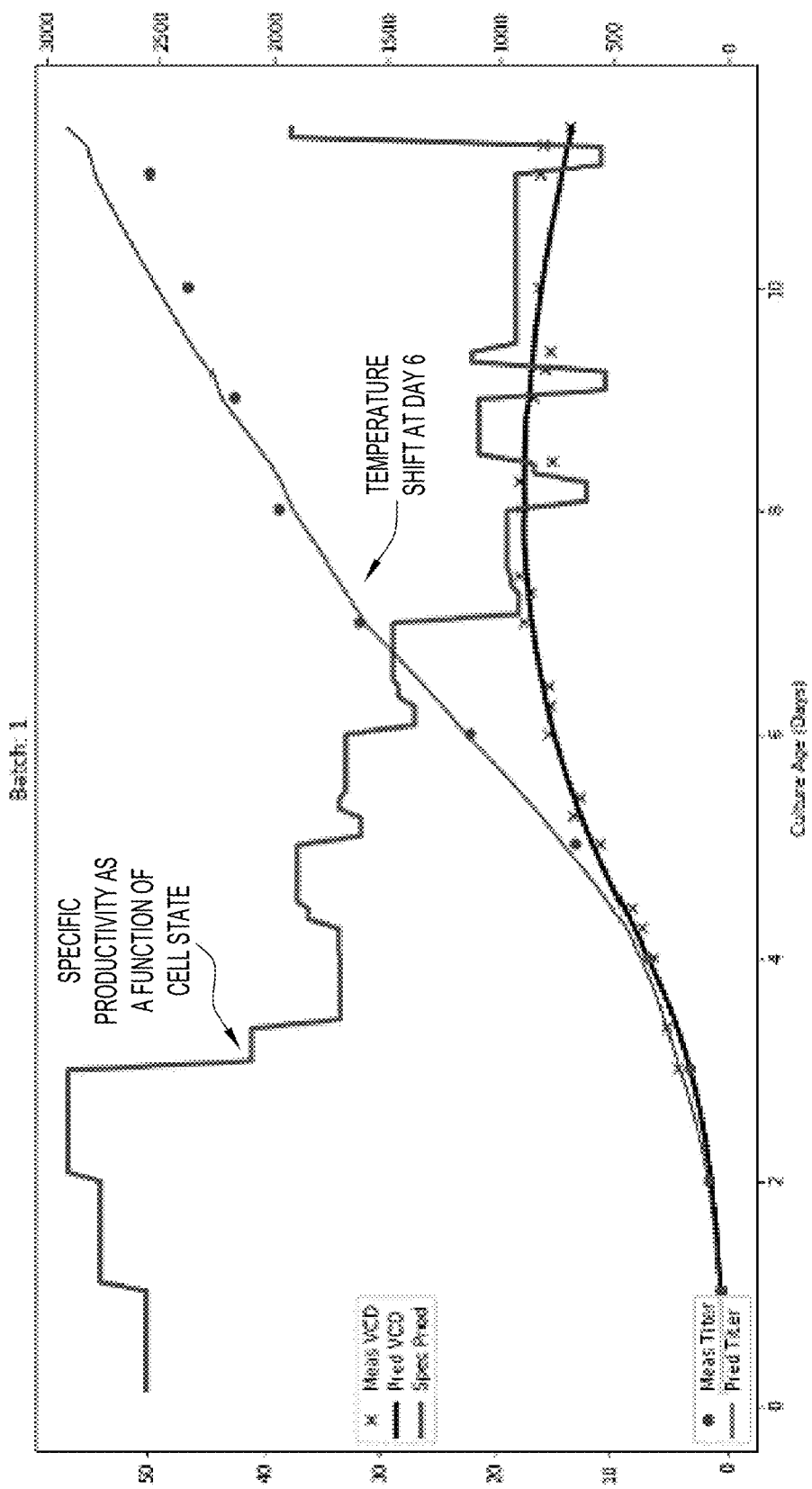
FIGS. 15A and 15B show additional examples of productivity and product quality according to the present disclosure.
Figure 15B:
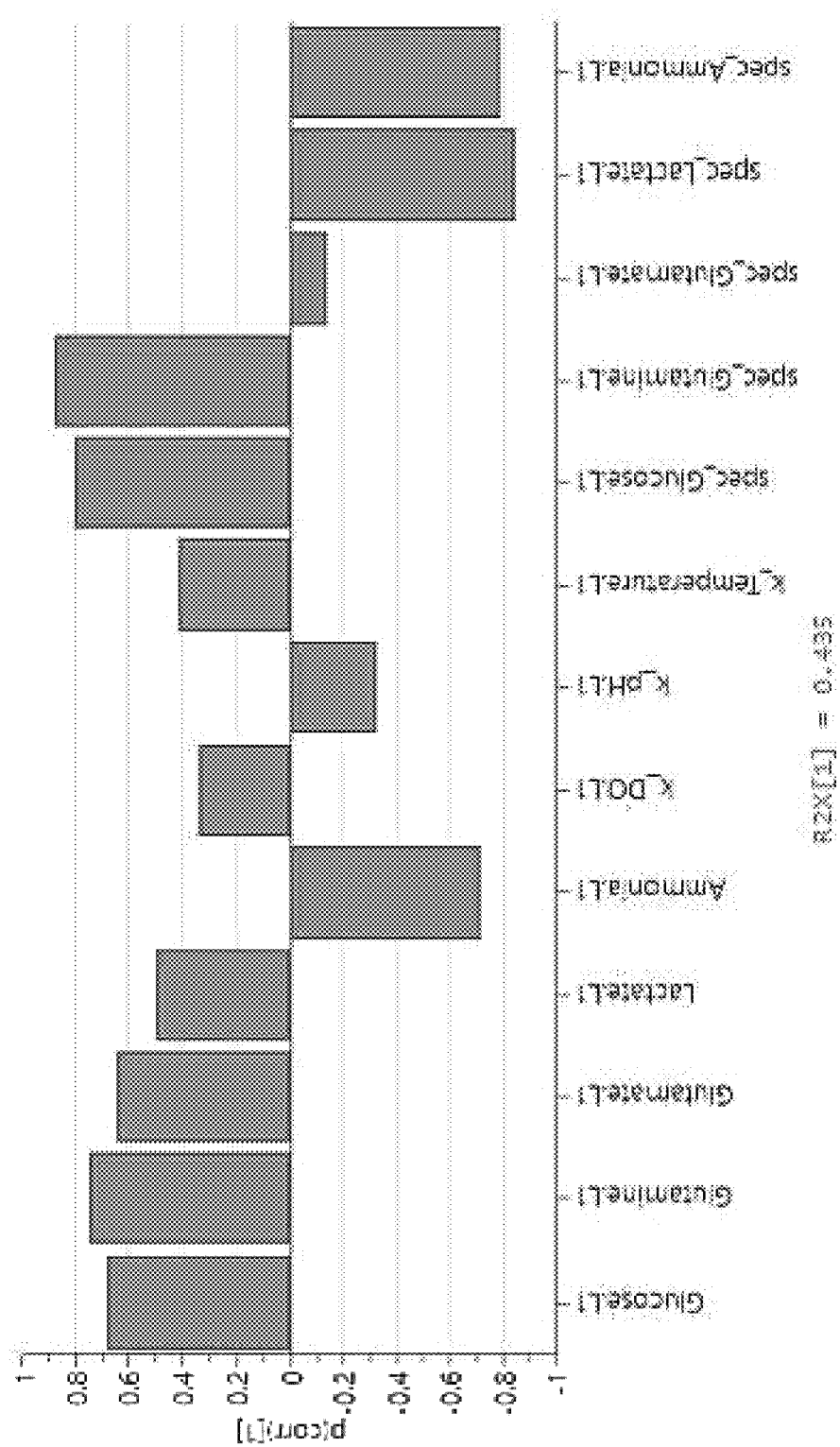

FIGS. 15A-15B show that growth rate is inhibited by cell density. For example, a cell density of about $12 \times 10^5$ begins to inhibit growth rate. The hybrid model allows the effects of cell density and lysed cells to be analyzed separately. Inhibition in growth may be explained by ammonia, which increases as cell density increases. However, dead cells that are lysed release toxins into the bulk fluid and further increase the cell death rate. Analysis of perfusion data may be used to separate these effects, since perfusion allows toxic metabolites to be removed, and removal of the toxins prevents an increase in cell death rate. Accordingly, these results show that the cell death rate is largely impacted by presence of lysed cells.

Figure 16:
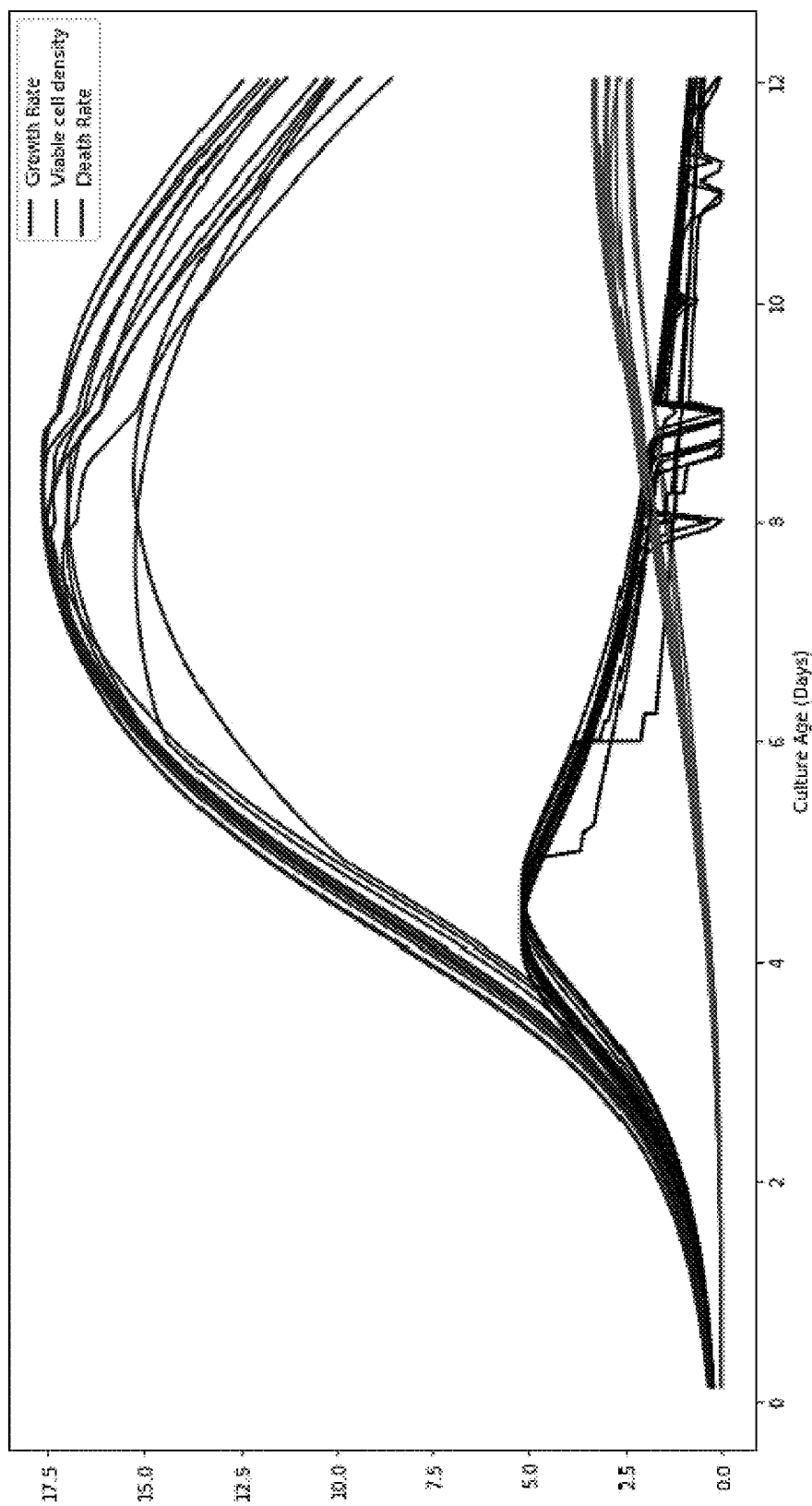
FIG. 16 shows examples of determining important unmeasured metabolic metrics from the Monod kinetic model. In this example, specific growth rate, specific death rate and the concentration of lysed cells (all unmeasured) are estimated from the Monod kinetic model according to the present disclosure.

FIG. 16 shows a plot of predicted VCD, growth rate, and death rate. This figure shows inhibition in growth (e.g., as cell densities increase, as metabolites accumulate, as nutrients deplete, as temperature shifts). Increases in the death rate occur as lysed cell density increases, ammonia is formed, and as pH shifts (small impact). Bolus feed additions correlate to a nutrient depletion that is very short lived. Growth inhibition is correlated with cell density.

Figure 17A:
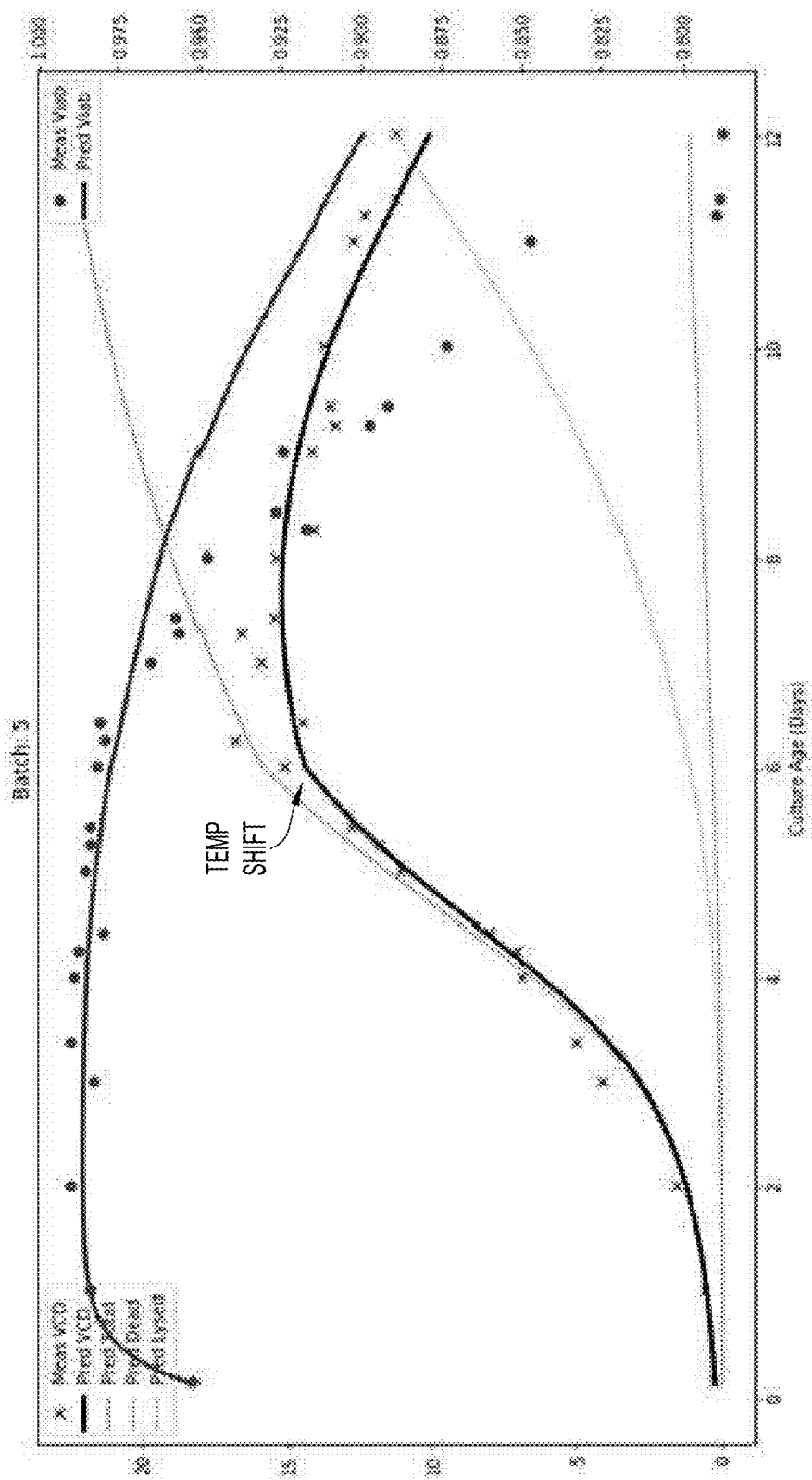
FIGS. 17A-17C show examples of the impact of independent variable adjustments to the growth profile according to the present disclosure. For each figure, the predicted profiles for growth states are shown in solid lines and associated data for measured states is included for comparison.
Figure 17B:
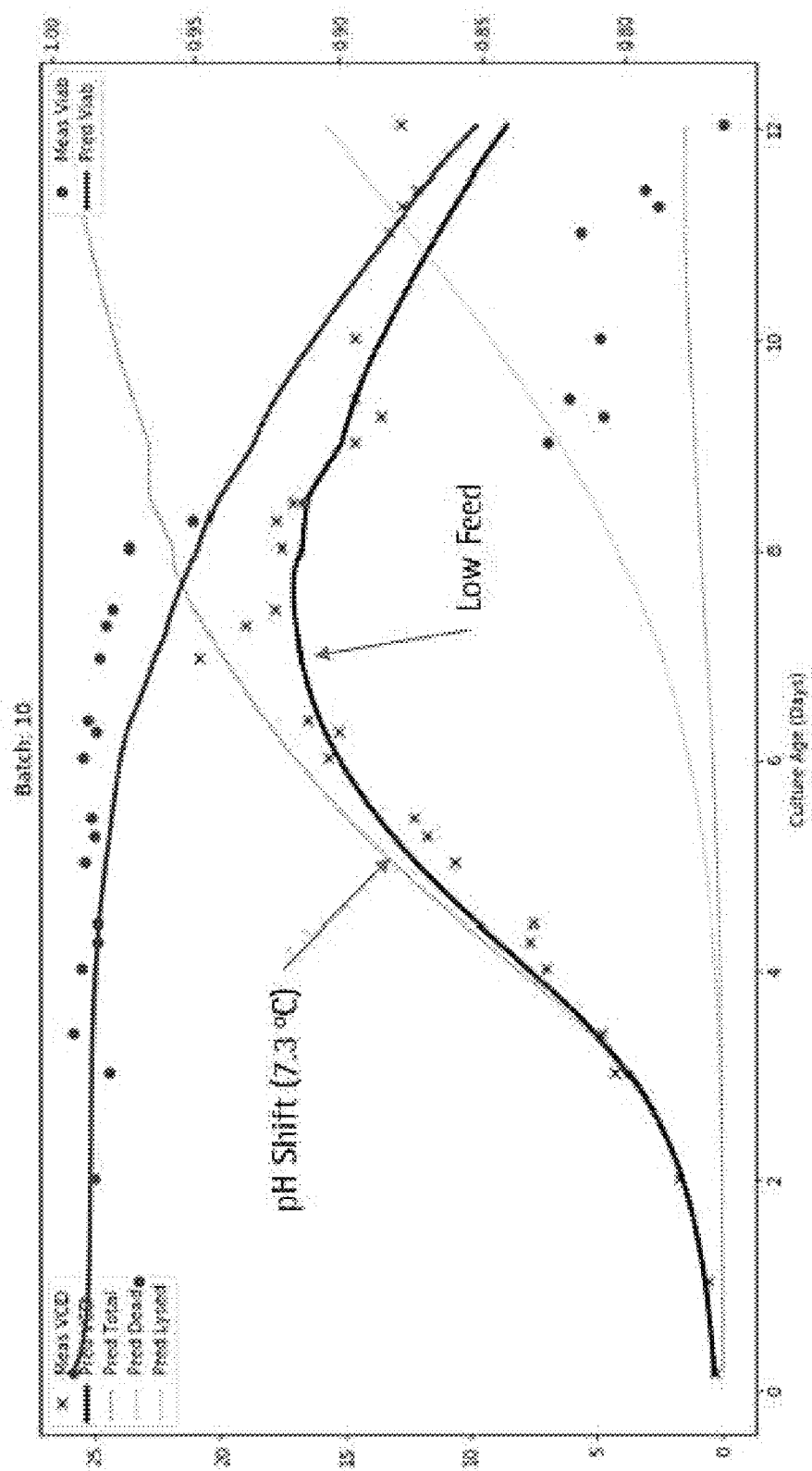
Figure 17C:
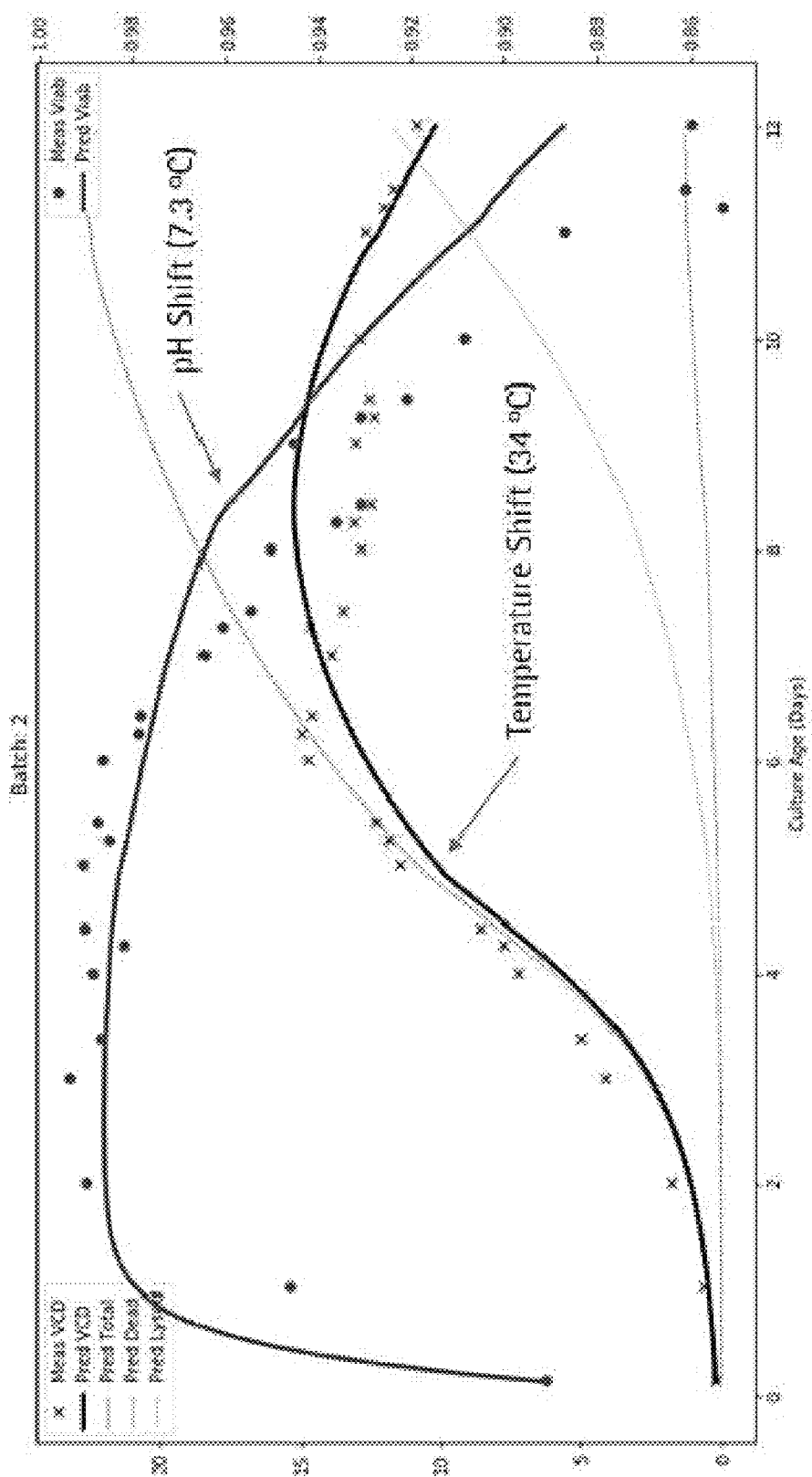

FIGS. 17A-17C show the effect of various changes in parameters. The predicted behavior of the hybrid growth model is compared to the measured experimental behavior. As shown in these figures, a shift in temperature is confirmed to inhibit growth. A pH shift appears to slightly increase cell death rates, but does not appear to inhibit growth rates. The cells seem to adapt and recover well from glucose and glutamine depletion. Therefore, no significant change is observed in growth, as the cells likely metabolize other carbon sources.

Growth profiles under various experimental conditions may be obtained using the following procedure:

1. Initialize the model (observer).
   Obtain starting conditions (e.g., VCD, Viability, Metabolites (glucose, glutamine, glutamate, lactate, ammonia, etc.), input parameters (temperature, pH, etc.).
2. Integrate the kinetic model over the time interval.

$$s_{k+\tau} = \int_k^{k+\tau} F(s, u) \quad (22)$$

3. Update metabolites and input parameters.
   Update the state estimates for metabolites based on mismatch between measured and estimated values. Update the input parameters to current measurements, and use a zero order hold over the sampling intervals.
4. Continue to step 2.

Growth profiles are influenced by input variable and metabolite trajectories. Unless otherwise indicated, estimates of the growth profiles (e.g., VCD, Viab, etc.) are not adjusted due to measured data. These results show good agreement between the measured and predicted growth profiles (e.g., VCD, Viab), indicating that the hybrid model accurately reflects the behavior of the cells in the bioreactor. Notably, the hybrid model accounts for predicted dead and lysed cells, which allows the hybrid model to accurately track the bioreactor at longer time scales than other models. The hybrid model allows the exploration of various parameters on the bioreactor system to determine how individual parameter changes affect the bioprocess.

Figure 18:
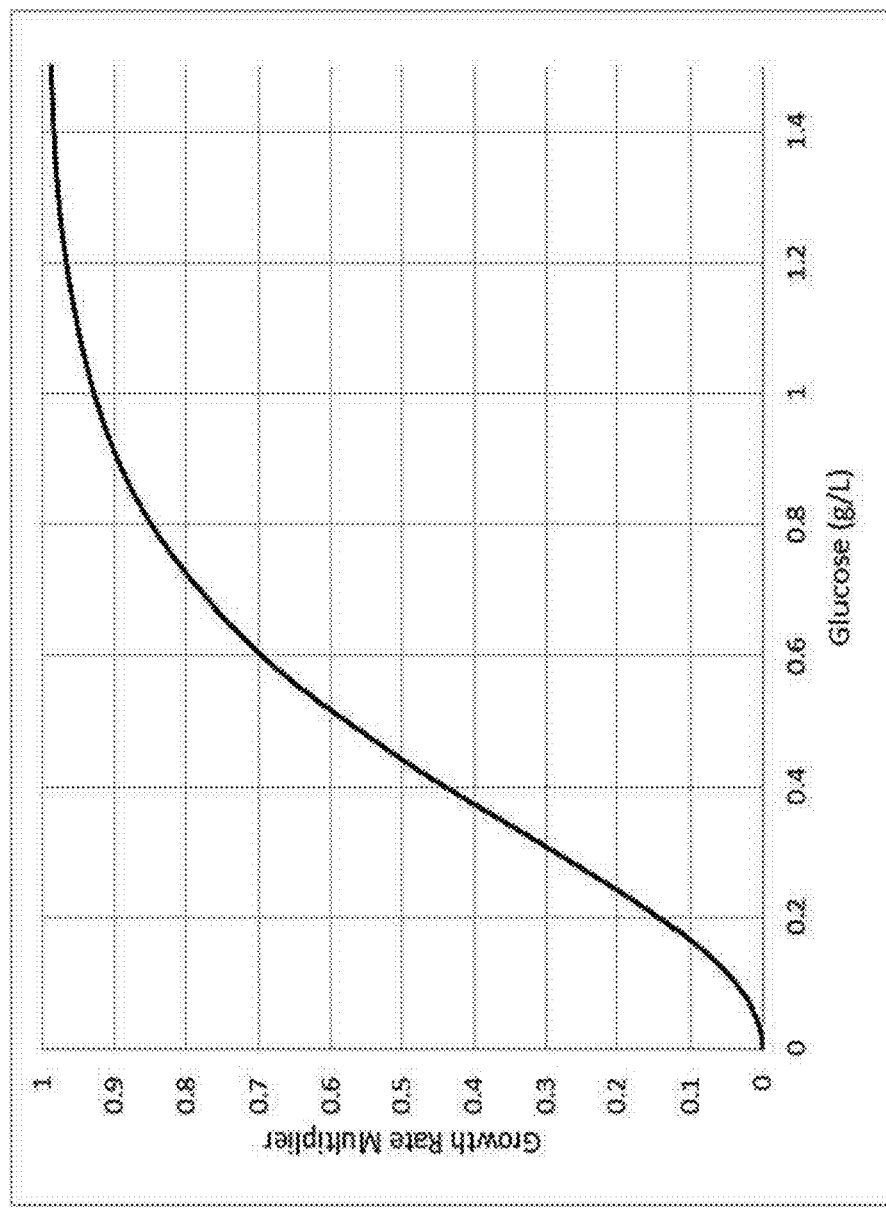
FIG. 18 shows the influence of substrates on the growth rate as described in eq. (6). This figure shows how the growth rate decreases when the substrate concentration falls below a threshold. In the example provided, the growth rate multiplier is shown for various glucose levels with a threshold value of 1 ($\theta_{s,i}=1$).

FIG. 18 shows another example of a parameter variation. In this example, growth is limited when substrates such as glucose are limited. This effect may be modeled by incorporating the following equations into the kinetic growth model.

$$u_{eff} = u_{max} \theta_{sub} \theta_{quad} \theta_{inh} \quad (25)$$

$$\theta_{sub} = \Pi \left[ \tanh\left(2\frac{[s_i]}{\theta_{s,i}}\right) \right]^2 \quad (26)$$

wherein $s_{glu}$: 1

Figure 19:
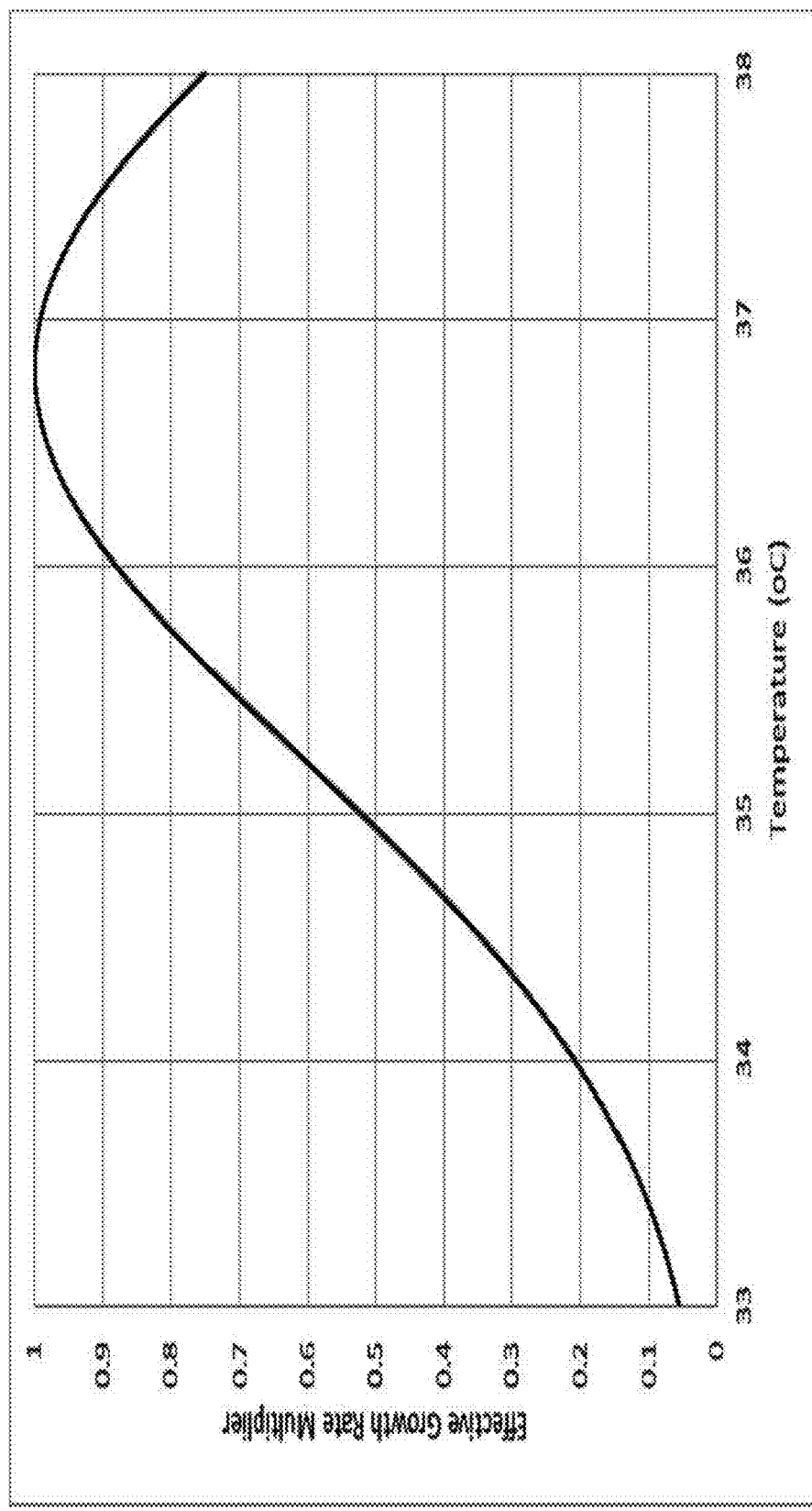
FIG. 19 shows the influence of a quadratic parameter on the effective growth rate described in eq. (7). The growth rate is decreased when the quadratic parameter is above or below a given optimum value ($\theta_{i,opt}=36.8°$ C.). The rate of decrease in growth rate is adjusted by the parameter, $\theta_{q,i}$.
Figure 20:
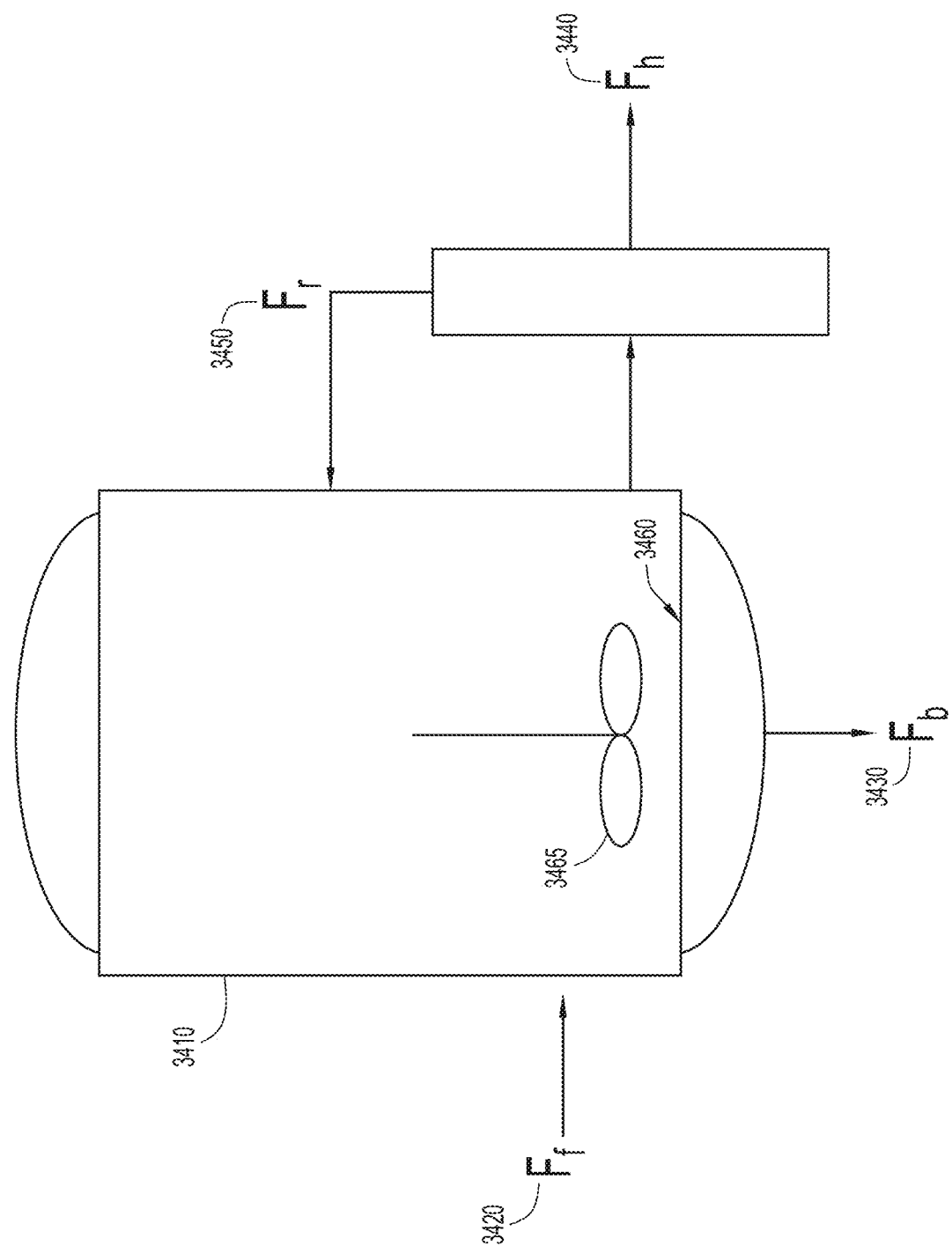
FIG. 20 is an illustration showing a system diagram of a bioprocess reactor, utilizing the hybrid model, according to the present disclosure. The figure depicts a continuously stirred tank reactor 3410 (with reaction stirrer 3465) with four flows. $F_f$ refers to the feed flow 3420, containing fresh media, $F_b$ is the bleed flow 3430, containing the same contents as the reactor, $F_h$, containing the bulk spent media 3440 in the reactor (the bulk fluid is separated from the cells by a divider 3460) and $F_r$, the recycle flow 3450, containing the cells and remaining bulk fluid in the complete recycle stream.

FIG. 19 shows experimental data demonstrating influence of quadratic type terms on growth rate. As the quadratic term deviates from its optimum, the growth rate is inhibited. Quadratic terms include temperature, pH, or other factors. This effect may be modeled by incorporating the following equations into the kinetic growth model.

$$u_{eff} = u_{max}\theta_{sub}\theta_{quad}\theta_{corr} \quad (27)$$

$$\theta_{quad} = \exp\left[-\frac{(q_i - \theta_{i,opt})^2}{\theta_{q,i}}\right]\phi_{pH,max} \quad (28)$$

wherein $\theta_{q,temp}$: 20, and $\theta_{temp,opt}$: 36.8

Figure 21:
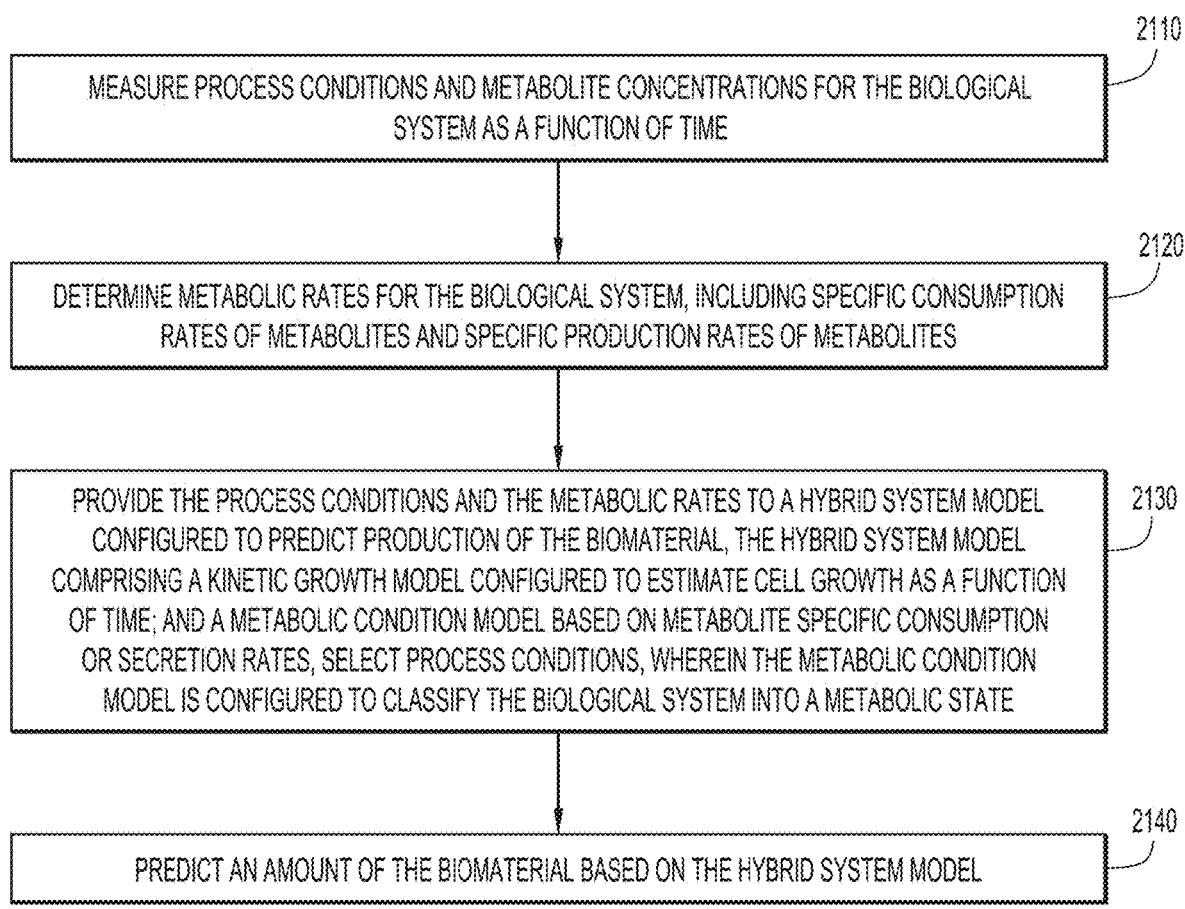
FIG. 21 is a high level flow diagram of operations of the hybrid model, according to the techniques provided herein.

FIG. 21 is a flow diagram of operations of the hybrid system model. At operation 2110, process conditions and metabolite concentrations for the biological system are measured as a function of time. At operation 2120, metabolic rates for the biological system are determined, including specific consumption rates of metabolites and specific production rates of metabolites. At operation 2130, the process conditions and the metabolic rates are provided to a hybrid system model configured to predict production of the biomaterial, the hybrid system model comprising a kinetic growth model configured to estimate cell growth as a function of time, and a metabolic condition model based on metabolite specific consumption or secretion rates, select process conditions, wherein the metabolic condition model is configured to classify the biological system into a metabolic state. At operation 2140, an amount of the biomaterial is predicted based on the hybrid system model.

Figure 22:
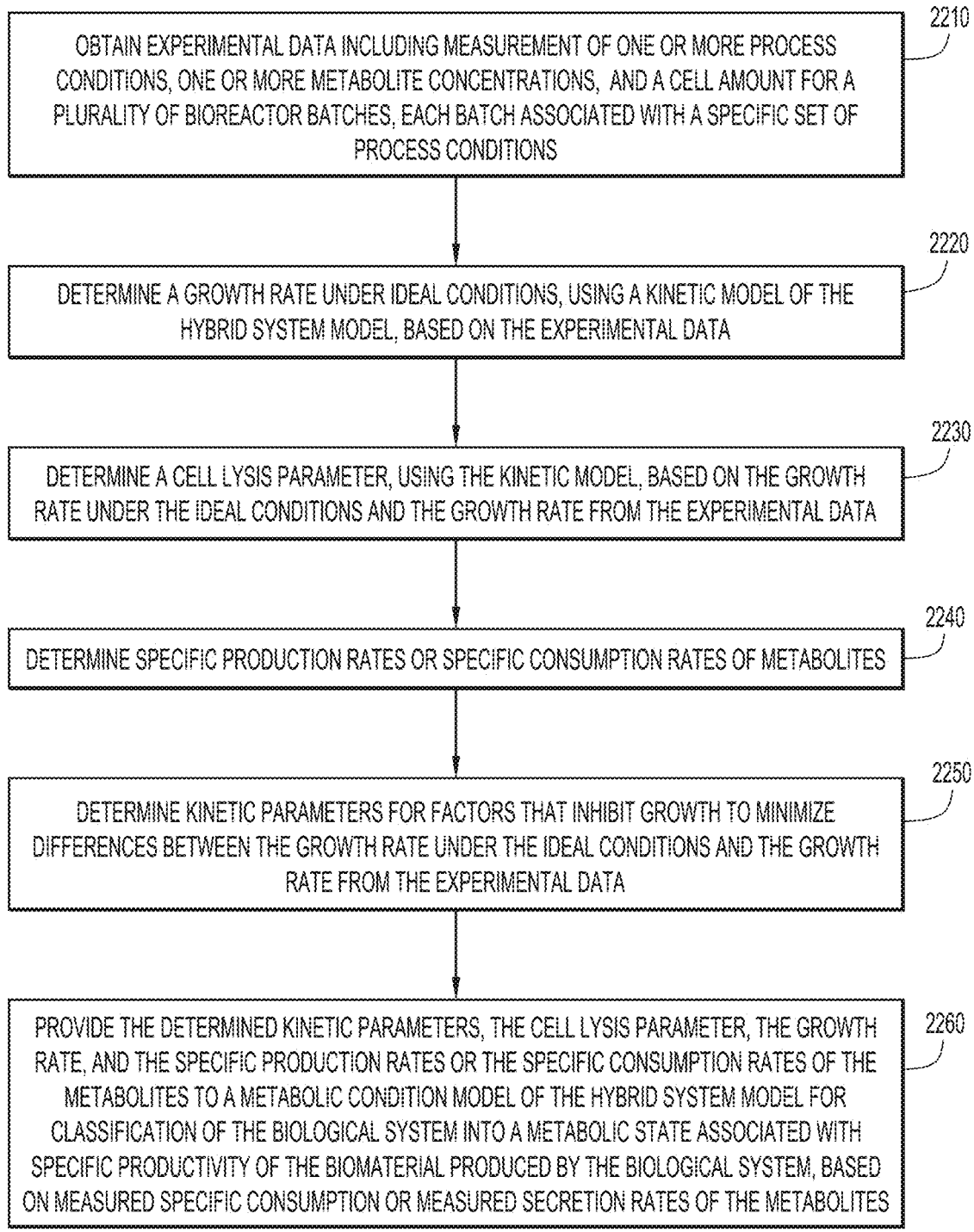
FIG. 22 is a high level flow diagram of operations to configure the hybrid model, according to the techniques provided herein.

FIG. 22 is a flow diagram of operations to configure the hybrid system model. At operation 2210, experimental data including measurement of one or more process conditions, one or more metabolite concentrations, and a cell amount for a plurality of bioreactor batches is obtained, each batch associated with a specific set of process conditions. At operation 2220, a growth rate is determined under ideal conditions, using a kinetic model of the hybrid system model, based on the experimental data. At operation 2230, a cell lysis parameter is determined, using the kinetic model, based on the growth rate under the ideal conditions and the growth rate from the experimental data. At operation 2240, specific production rates or specific consumption rates of metabolites are determined. At operation 2250, kinetic parameters for factors that inhibit growth are determined, to minimize differences between the growth rate under the ideal conditions and the growth rate from the experimental data. At operation 2260, the determined kinetic parameters, the cell lysis parameter, the growth rate, and the specific production rates or the specific consumption rates of the metabolites are provided to a metabolic condition model of the hybrid system model for classification of the biological system into a metabolic state associated with specific productivity of the biomaterial produced by the biological system, based on measured specific consumption or measured secretion rates of the metabolites.

Based on the hybrid model, the parameters of the bioreactor may be tuned to optimize titer. These techniques are compatible with simulation, optimization, process monitoring (state observation).

The techniques provided herein provide models which accurately mimic cell behavior in a bioreactor. As shown by the experimental data, the predicted VCD and viability profiles match the measured experimental values for various feed, pH, and temperature profiles.

Additionally, the hybrid model effectively acts as a soft sensor for cell metabolism and metabolites, allowing monitoring and characterization of metabolite specific consumption and production, as well as monitoring and characterization of changes in cell state and metabolic activity.

Unlike other models, which do not estimate or otherwise account for lysed cells, the hybrid model takes into account the number of lysed cells, which influences bulk fluid toxicity. This approach allows the hybrid model to be more accurate than other models that do not account for this feature, and at longer time scales than other models.

Other advantages of the hybrid model include having an increased knowledge of cell metabolism and of factors that drive cell growth, cell death, viability, titer and product quality. The hybrid model also provides the ability to simulate performance of new process conditions (e.g., feeding, temp, pH profiles, etc.) to maximize productivity and to observe cell state (e.g., metabolic activity, etc.) or changes thereof. In other aspects, perfusion performance may be predicted from fed batch operation.

These techniques provide for improved forecasting, improved prediction of titer, and product quality based on monitoring and prediction. Present techniques are applicable to a wide variety of application areas including a simple univariate metabolite state estimator, a comprehensive multivariate metabolite state estimator, live systems (e.g., digital twin simulation), etc. Accordingly, present techniques are in an improvement in the field of bioreactor control and biologics manufacturing.

Returning to FIG. 1, an exemplary hardware configuration of a computing system that may be used to implement at least a part of the system 100 as described herein is provided. Server systems 10 include a central processing unit (CPU) 16, a system memory 17, network interface 18, and user interface 19. These components of the computer are coupled to each other, e.g., via a system bus (not shown). The CPU 16 may perform arithmetic, logic and/or control operations by accessing the system memory 17. The CPU 16 may comprise a plurality of processors (e.g., cores) that can perform parallel processing, which may lead to higher performance of the computing system 100. The CPU 16 may implement the processors, engines, and modules of the exemplary devices and/or system described in FIGS. 1 and 2, as well as other figures. The system memory 17 may store information and/or instructions for use in combination with the CPU 16. The system memory 17 may include volatile and non-volatile memory, such as a random access memory (RAM) and a read only memory (ROM). A basic input/output system (BIOS) containing the basic routines that transfers information between elements within the server systems 10, such as during start-up, may be stored in the memory 17 (e.g., ROM). The system bus may be any of several types of bus structures including a memory bus or memory controller, a peripheral bus, and a local bus using any of a variety of bus architectures. The computer may include a network interface 18 for communicating with other computers (e.g., client systems 20) and/or devices via a network (e.g., network 45).

Further, the computer may include a hard disk drive (HDD) for reading from and writing to a hard disk (not shown), and an external disk drive (not shown) for reading from or writing to a removable disk (not shown). The removable disk may be a magnetic disk for a magnetic disk drive or an optical disk such as a CD ROM for an optical disk drive. The HDD and the external disk drive are connected to the system bus by a HDD interface and an external disk drive interface, respectively. The drives and their associated computer-readable media provide non-volatile storage of computer-readable instructions, data structures, program modules and other data for the general purpose or specific purpose computer. The data structures may include relevant data for the implementation of the exemplary method and its variations as described herein. The relevant data may be organized in a database, for example, a relational or object database.

Although the exemplary environment described herein employs a hard disk (not shown) and an external disk (not shown), it should be appreciated by those skilled in the art that other types of computer readable media which can store data that is accessible by a computer, such as magnetic cassettes, flash memory cards, digital video disks, random access memories, read only memories, and the like, may also be used in the exemplary operating environment.

A number of program modules may be stored on the hard disk, external disk, ROM or RAM, including an operating system (not shown), one or more application programs, other program modules (not shown), and customized software (e.g., kinetic growth model 50, metabolic condition model 60, state correction module 75, process monitoring engine 80, flagging and alerts engine 85, consumption rate and secretion rate module 90, etc.). The application programs may include at least a part of the functionality as described above.

In addition or as an alternative to an implementation using server systems 10 as shown in FIG. 1, a part or all of the functionality of the exemplary embodiments described herein may be implemented as one or more hardware circuits. Examples of such hardware circuits may include but are not limited to: Large Scale Integration (LSI), Reduced Instruction Set Circuits (RISC), Application Specific Integrated Circuit (ASIC) and Field Programmable Gate Array (FPGA).

Database 30 may store various information for the techniques provided herein, such as training data 32, process conditions 34, and output data 36, or any other data generated by the kinetic and metabolic state observation system in a test or real environment. The database system 30 may be local to or remote from server systems 10 and client systems 20 and may communicate via any suitable communication medium, such as a local area network (LAN), a wide area network (WAN), Internet, Intranet, hardwire, wireless link, etc.

Client systems 20 may be implemented by any suitable computer systems preferably equipped with a display or monitor, at least one hardware processor (e.g., microprocessor, controller, central processing unit (CPU), GPU, etc.), one or more memories, and/or internal or external network interfaces or communications devices, such as a modem, a network card, etc.). The system may further comprise optional input devices, such as a keyboard, a mouse or another input device, as well as any commercially available and custom software. For example, in FIG. 1, the client includes at least one CPU/processor 22, one or more memories 24, and/or internal or external network interfaces or communications devices 26 such as a modem or network cards, and a user interface 28, etc. The optional input devices may include a keyboard, mouse, or other input device. Client system 20 may solicit information from a user to be provided to servers systems 10. The client systems may present a graphical user interface, such as a GUI, etc., or other interface, such as command line prompts, menu screens, etc., to obtain information from users for operating a bioprocess reaction and to monitor the bioprocess reaction using the kinetic and metabolic state observation system.

The present invention embodiments may be generally applicable to providing support in any context, and is not limited to any particular application domain, such as bioreactor manufacturing, health, etc.

The description provided herein has been presented for purposes of illustration and description, and is not intended to be exhaustive or limited by the examples disclosed herein. Many modifications and variations will be apparent to one of ordinary skill in the art without departing from the scope and spirit of the techniques provided herein. The selected examples were chosen to best explain the principles of operation and components of the metabolic state observer, and to enable those of ordinary skill in the art to understand the various embodiments contemplated herein.

Aspects of the kinetic and metabolic state observation system are described herein with reference to flowchart illustrations and/or block diagrams of methods, apparatus (systems), and computer program products. Each block of the flowchart illustrations and/or block diagrams, and combinations of blocks in the flowchart illustrations and/or block diagrams, may be implemented by computer readable program instructions. Each block of the block diagrams and/or flowchart illustrations, or combination thereof, may be implemented by special purpose software-based systems that perform the specific functions to carry out combinations of special purpose computer instructions disclosed herein.

GLOSSARY $F_b$: Cell bleed flow rate
$F_f$: Flow rate of the feed containing fresh media
$F_h$: Harvest flow rate
$k_d$: Death rate in the absence of lysed cells
$k_l$: Rate of conversion of dead cells to lysed cells
$k_t$: Increase in death rate due to lysed cell concentration
IgG: Biomaterial, in this case, an immunoglobulin $$\frac{dIgG}{dt}:$$

Rate of change of the biomaterial as a function of time
$I_i$: Value of the inhibition variable, which may be a metabolite or independent variable
$mAdd_{(i,k)}$: Bolus or continuous feed addition of the metabolite i between the time interval t=k and t=k+1

$$\frac{dm_i}{dt}:$$

Rate of change of a metabolite
$m_{r,i}$: Concentration of a metabolite in the bioreactor
$m_{f,i}$: Concentration of a metabolite in the feed
$m_i$: Specific metabolite
Qp: Function with inputs comprising metabolite concentrations m
$q_i$: Value of the quadratic variable, which may be a metabolite or independent variable
$s_i$: Substrate value, which may be a metabolite or independent variable
$u_d$: Cell death rate
u: Independent variables
$u_{max}$: Maximum growth rate (under optimal conditions)
VCD: Viable cell density
iVCD: Integrated VCD over a time step
V: Volume of the material in the bioreactor $$\frac{dx_v}{dt}:$$

Change in viable cell density as a function of time $$\frac{dx_l}{dt}:$$

Change in lysed cell density as a function of time $$\frac{dx_d}{dt}:$$

Change in dead cell density as a function of time
- $x_t$: Total cell density
- $x_v$: Viable cell density
- $x_d$: Dead cell density
- $x_l$: Lysed cell density
- $\theta_i$: Coefficient related to inhibition in growth rate from ideal conditions
- $\theta_{i,i}$: Coefficient representing the value of the inhibition variable above which growth is inhibited
- $\theta_{i,opt}$: Coefficient representing the value of the quadratic variable where growth is maximized
- $\theta_{inh}$: Inhibition in growth due to the excess amount of a biomaterial
- $\theta_{q,i}$: Coefficient representing the sensitivity of the growth inhibition
- $\theta_{quad}$: Reduction in growth rate due to quadratic terms (e.g., temp, pH, etc.)
- $\theta_{s,i}$: Coefficient representing the substrate concentration below which growth is inhibited
- $\theta_{sub}$: Reduction in growth rate due to substrate depletion
- $\theta_{inh}$: Population density
- $\mu_{eff}$: Effective growth rate
- $\delta_{m,i}(t)$: Specific consumption or secretion rate of a metabolite at the current time

The invention claimed is:

1. A method for predicting an amount of at least one biomaterial produced or consumed by a biological system in a bioreactor comprising:
   measuring process conditions and metabolite concentrations for the biological system as a function of time;
   determining metabolic rates for the biological system, including specific consumption rates of metabolites and specific production rates of metabolites;
   providing the process conditions and the metabolic rates to a hybrid system model configured to predict production of the biomaterial, the hybrid system model comprising:
      a kinetic growth model configured to estimate cell growth as a function of time; and
      a metabolic condition model based on metabolite specific consumption or secretion rates, select process conditions, wherein the metabolic condition model is configured to classify the biological system into a metabolic state; and
   predicting an amount of the biomaterial based on the hybrid system model.

2. The method of claim 1, wherein the kinetic growth model is further configured to estimate cell viability.

3. The method of claim 1, wherein the kinetic growth model is further configured to account for lysed cells.

4. The method of claim 1, further comprising:
   constructing a metabolic state observer for a metabolite to provide an estimate of an internal metabolic state of the biological system.

5. The method of claim 4, further comprising:
   obtaining a current measurement of the metabolite;
   determining a consumption rate for the metabolite using the metabolic state observer; and
   predicting a future concentration of the metabolite using the metabolic state observer and the current measurement.

6. The method of claim 4, further comprising:
   performing cell state classification using the metabolic state observer to estimate specific consumption rates or specific production rates for the metabolite.

7. The method of claim 6, wherein the estimated specific consumption rates or the estimated specific production rates are determined using training data.

8. The method of claim 4, further comprising:
   classifying the internal metabolic state into an optimal or a suboptimal category for biomaterial production; and
   sending a notification to a user, when the internal metabolic state is classified into a suboptimal category.

9. The method of claim 1, wherein the kinetic growth model comprises a monod kinetic model or a saturation kinetic model.

10. The method of claim 1, further comprising measuring cell density or cell viability for the biological system as a function of time.

11. The method of claim 1, wherein the kinetic growth model is further configured to estimate microbial cell growth as a function of time.

12. The method of claim 1, wherein the metabolic condition model comprises one or more of a machine learning model, a deep learning model, a principal component analysis (PCA) model, a partial least squares (PLS) model, a partial least squares discriminant analysis (PLS-DA) model, and an orthogonal partial least squares discriminant analysis (OPLS-DA) model.

13. The method of claim 1, further comprising:
   obtaining a test sample from the bioreactor; and
   determining whether the amount of the biomaterial in the test sample is within a range predicted by the hybrid system model.

14. The method of claim 1, further comprising updating parameters of the hybrid system model when the hybrid system model is in operation, wherein the parameters include the metabolic rates and coefficients associated with the hybrid system model.

15. The method of claim 1, wherein the process conditions include one or more of pH, temperature, dissolved oxygen, osmolality, process flow leaving the bioreactor, growth media, by-products, amino acids, metabolites, oxygen flow rate, nitrogen flow rate, carbon dioxide flow rate, air flow rate, and agitation rate.

16. The method of claim 15, wherein the growth media comprises nutrients including an amino acid, a saccharide, or an organic acid.

17. The method of claim 15, wherein the by-products include an amino acid, a saccharide, an organic acid, or ammonia.

18. The method of claim 1, further comprising at least one of:
   determining optimal process conditions for the bioreactor based on the hybrid system model;
   measuring experimental process conditions of the bioreactor using one or more sensors as a function of time;
   monitoring the measured experimental process conditions to detect deviations from the optimal process conditions; and when a deviation is detected, sending a notification to a user.

19. The method of claim 1, further comprising at least one of:
- determining optimal process conditions for the bioreactor based on the hybrid system model;
- measuring experimental process conditions of the bioreactor using one or more sensors as a function of time;
- monitoring the measured experimental process conditions to detect deviations from the optimal process conditions; and
- providing feedback to a controller controlling the bioreactor to automatically adjust the experimental process conditions to minimize deviation from the optimal process conditions.

20. The method of claim 1, further comprising:
- simulating, using the hybrid system model, a predicted amount of at least one biomaterial, wherein the hybrid system model is initialized with the process conditions; and
- determining one or more states of the biological system based on the simulation.

21. The method of claim 20, wherein the simulating further comprises:
- adjusting the process conditions based on an optimization method to determine a set of process conditions that optimize predicted trajectories, product quantity (titer), and/or product quality.

* * * * *